(12) United States Patent
Grüner et al.

(10) Patent No.: US 11,571,194 B2
(45) Date of Patent: Feb. 7, 2023

(54) ENDOSCOPIC DEVICE

(71) Applicant: KARL STORZ SE & Co. KG, Tuttlingen (DE)

(72) Inventors: Sven Grüner, Tuttlingen (DE); Jochen Stefan, Tuttlingen (DE)

(73) Assignee: KARL STORZ SE & CO. KG, Tuttlingen (DE)

(*) Notice: Subject to any disclaimer, the term of this patent is extended or adjusted under 35 U.S.C. 154(b) by 58 days.

(21) Appl. No.: 16/984,574

(22) Filed: Aug. 4, 2020

(65) Prior Publication Data
US 2021/0038208 A1 Feb. 11, 2021

(30) Foreign Application Priority Data

Aug. 5, 2019 (DE) .................. 10 2019 121 037.2

(51) Int. Cl.
*A61B 17/00* (2006.01)
*A61B 34/30* (2016.01)
(Continued)

(52) U.S. Cl.
CPC ........ *A61B 17/00234* (2013.01); *A61B 34/30* (2016.02); *A61B 34/37* (2016.02);
(Continued)

(58) Field of Classification Search
CPC combination set(s) only.
See application file for complete search history.

(56) References Cited

U.S. PATENT DOCUMENTS

2006/0111210 A1* 5/2006 Hinman ........... A61B 17/07207
474/206
2010/0116081 A1* 5/2010 Pistor ..................... B25J 9/0012
264/334
(Continued)

OTHER PUBLICATIONS

Search Report for EP 20189284.1 (in German), dated Nov. 12, 2020 (8 pp.).
(Continued)

*Primary Examiner* — Gary Jackson
*Assistant Examiner* — Zahed Kabir
(74) *Attorney, Agent, or Firm* — Eversheds Sutherland (US) LLP

(57) ABSTRACT

This application provides an endoscopic device having at least one shaft with at least one portion deflectable, and having at least one deflection mechanism, which is configured to deflect the deflectable portion and includes at least one first connection member and at least one second connection member. When the connection members are arranged in a straight position relative to each other, a straight-position spacing exists defined by a shortest connection between a geometric midpoint of the first connection member and a geometric midpoint of the second connection member and, when the connection members are arranged in a deflection position relative to each other, a deflection-position spacing exists which is defined by a shortest connection between a geometric midpoint of the first connection member and a geometric midpoint of the second connection member, and the deflection-position spacing in the deflection position is greater than the straight-position spacing in the straight position.

14 Claims, 17 Drawing Sheets

Figure 1:
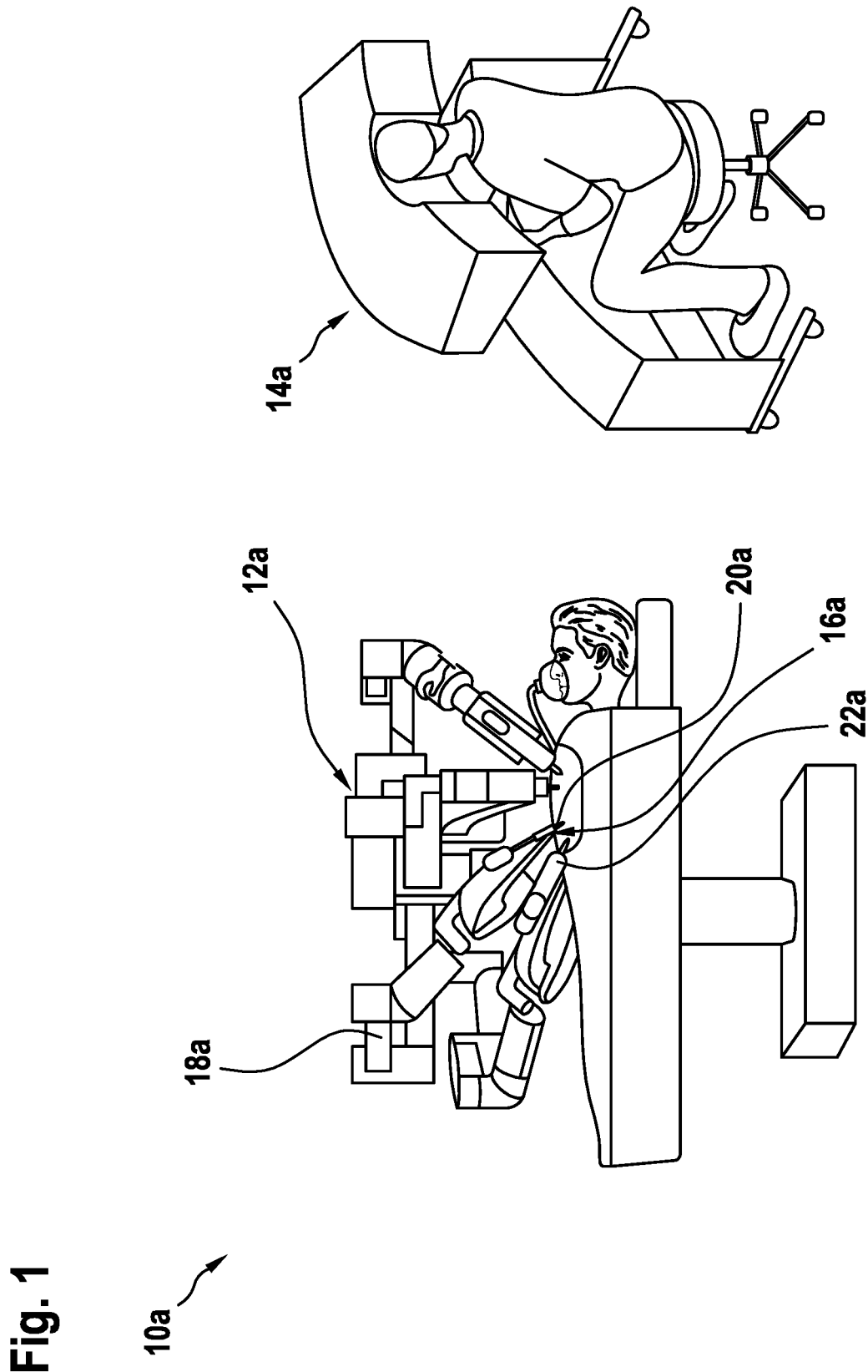

(51) Int. Cl.
*A61B 34/37* (2016.01)
*A61B 17/29* (2006.01)

(52) U.S. Cl.
CPC ............... *A61B 2017/00314* (2013.01); *A61B 2017/00526* (2013.01); *A61B 2017/2905* (2013.01); *A61B 2034/301* (2016.02)

(56) References Cited

U.S. PATENT DOCUMENTS

| | | | |
|---|---|---|---|
| 2011/0295065 A1* | 12/2011 | Gurusamy | A61B 1/0057 600/141 |
| 2012/0123395 A1* | 5/2012 | Stoy | A61B 34/72 606/1 |
| 2015/0032150 A1 | 1/2015 | Ishida et al. | |
| 2015/0150633 A1 | 6/2015 | Castro et al. | |

OTHER PUBLICATIONS

Search Report for DE 10 2019 121 037.2, dated Apr. 22, 2020 (10 pp.).

* cited by examiner

ENDOSCOPIC DEVICE

PRIOR ART

The invention relates to an endoscopic device according to the preamble of claim 1, to an endoscope and/or endoscopic instrument having an endoscopic device, according to claim 11, to a surgical system having an endoscopic device, according to claim 12, and to a method for operating and/or producing an endoscopic device, according to claim 13.

An endoscopic device has already been proposed having at least one shaft, which has at least one portion deflectable in at least one plane, and having at least one deflection mechanism, which is configured to deflect the deflectable portion and comprises, arranged in series, at least one first connection member and at least one second connection member interacting for a deflection with the first connection member.

The object of the invention is in particular to make available a device of this kind which has improved properties in terms of its functionality According to the invention, the object is achieved by the features of claims 1, 11, 12 and 13, while advantageous embodiments and developments of the invention are set forth in the dependent claims.

Advantages of the Invention

The invention proceeds from an endoscopic device having at least one shaft, which has at least one portion deflectable in at least one plane, and having at least one deflection mechanism, which is configured to deflect the deflectable portion and comprises, arranged in series, at least one first connection member and at least one second connection member interacting for a deflection with the first connection member.

In one aspect of the invention, which can be considered in particular in combination with further aspects of the invention, it is proposed that, when the first connection member and the second connection member are arranged in a straight position relative to each other, a straight-position spacing exists which is defined by a shortest connection between a geometric midpoint of the first connection member and a geometric midpoint of the second connection member, and, when the first connection member and the second connection member are arranged in a deflection position relative to each other, a deflection-position spacing exists which is defined by a shortest connection between a geometric midpoint of the first connection member and a geometric midpoint of the second connection member, and the deflection-position spacing of the connection members in the deflection position is greater than the straight-position spacing of the connection members in the straight position.

In this way, a functionality of the endoscopic device can advantageously be improved. It is advantageously possible to avoid a situation where connection members of the deflection mechanism are arranged randomly in relation to each other upon a return of the deflectable portion from a basic deflection position. Instead, it is possible to achieve an automatic return of the connection members to their basic position in the manner of a self-alignment. It is thus advantageously possible to avoid a situation where connection members arranged randomly in relation to each other impede a function of the endoscopic device and/or cause injury to a patient, for example if the endoscopic device has to be inserted into a patient and/or extracted from the latter in an emergency.

An "endoscopic device" should be understood in particular to mean a constituent part, preferably a functional constituent part, in particular a subassembly and/or a structural component and/or functional component of an endoscopic instrument and/or of an endoscope. Alternatively, the endoscopic device can at least partly, preferably at least largely and particularly preferably completely embody an endoscope and/or an endoscopic instrument. "Endoscopically" should be understood in particular as also meaning minimally invasive. The expression "at least largely" should be understood to mean in particular at least 55%, preferably at least 65%, preferably at least 75%, particularly preferably at least 85%, and very particularly preferably at least 95%, or advantageously completely, to be precise in relation to a volume and/or mass of an object, in particular. The endoscopic device is, for example, configured to be introduced, at least partly and preferably at least largely, into an orifice, in particular an artificial and/or natural orifice, in particular a body orifice, in order to perform a treatment and/or observation there. An endoscopic instrument can, for example, be in the form of endoscopic forceps, endoscopic scissors, an endoscopic scalpel, an endoscopic stapler or the like. It is conceivable that the endoscopic device is configured to provide at least one, two or more electrical potentials, for example in order for tissue to be cut, sealed, coagulated and/or the like. In particular, "configured" should be understood to mean specifically programmed, provided, designed and/or equipped. An object being configured for a specific function should be understood to mean in particular that the object satisfies and/or carries out this specific function in at least one application state and/or operational state. If the endoscopic device has for example at least one shaft, the latter is configured to be introduced, at least partly and preferably at least largely, into an orifice, in particular an artificial and/or natural orifice, in particular a body orifice. The shaft comprises for example at least one end portion and/or further end portion, wherein for example the end portion is a distal end portion and/or the further end portion is a proximal end portion. "Distal" should be understood in particular to mean facing a patient and/or distant from a user during operation. "Proximal" should be understood in particular to mean distant from a patient and/or facing a user during operation. The shaft has for example an axis of principal extent. An axis of principal extent of an object should be understood as an axis which runs through the geometric midpoint and/or center of gravity of the object and is at least substantially parallel to a direction of principal extent of the object. Here, a "direction of principal extent" of an object should be understood in particular to mean a direction that extends parallel to a longest edge of a smallest imagined cuboid that just still completely surrounds the object. A longitudinal extent for example of the shaft is identical to the direction of principal extent of the latter. Here, "at least substantially parallel" should be understood in particular as an orientation of a direction relative to a reference direction, in particular in a plane, wherein the direction and the reference direction enclose an angle of 0° in particular in consideration of a maximum deviation of less than 8°, advantageously of less than 5° and particularly advantageously of less than 2°. A width can be measured at least substantially perpendicular to the longitudinal extent. Here, "at least substantially perpendicular" should be understood in particular as an orientation of a direction relative to a reference direction, in particular in a plane, wherein the direction and the reference direction enclose an angle of 90°, in particular in consideration of a maximum deviation of less than 8°, advantageously of less than 5° and particularly advantageously of less than 2°. The endoscopic device can have a plurality of components that can be at least substantially identical to one another. "At least substantially identical" should be understood to mean either identical or identical apart from assembly and/or production tolerances. The endoscopic device can be designed integrally at least in part. The fact that "an object and a further object have an at least partly integral embodiment/connection" should be understood to mean in particular that at least one element and/or part of the object and at least one element and/or part of the further object have an integral embodiment/connection. In particular, "integral" should be understood to mean at least cohesively bonded, for example by a welding process, an adhesive bonding process, a spraying process and/or any other process appearing expedient to a person skilled in the art. "Integral" should be understood in particular as meaning formed in one piece, for example by production from one cast and/or by production in a single-component or multiple-component injection method and, advantageously, from a single blank. Components of the endoscopic device should be connected to one another at least partially by form-fit and/or force-fit engagement. Here, "force-fit and/or form-fit engagement" should be understood in particular as meaning connected, preferably releasably connected, wherein a holding force is transmitted between two objects preferably by geometric interlocking of the structural components in one another and/or by a frictional force that preferably acts between the objects. Alternatively or in addition, components of the endoscopic device can be connected to one another by cohesive bonding. "Cohesive bonding" should be understood in particular as meaning that the objects are held together by atomic or molecular forces, for example by soldering, welding, adhesion and/or vulcanization. Moreover, the endoscopic device can be part of a surgical system. A surgical system should be understood in particular as a system configured for performing a surgical procedure, for example an endoscopic and/or minimally invasive procedure, which system comprises at least one surgical robot. The surgical robot can comprise at least one surgical robot arm or a plurality of surgical robot arms. The endoscopic device can be controllable and/or actuatable by the surgical robot, in particular the surgical robot arm. The endoscopic device can be able to be coupled releasably to the surgical robot, for example in order to permit exchange and/or cleaning of the endoscopic device. Moreover, the surgical system can comprise at least one controller, which is configured for manual and/or automated control of the surgical robot.

The shaft can have a deflectable portion. For the deflection of the shaft, the endoscopic device can have at least one deflection mechanism. The deflection mechanism is designed in particular for a mechanical deflection of the deflectable portion of the shaft. The shaft is deflectable in particular in at least one further plane, which is different from the at least one plane. For example, the further plane can be perpendicular to the plane. It is moreover conceivable that the shaft is deflectable along its circumference in any desired planes.

In particular, the deflection mechanism can comprise at least one and preferably several first connection members, which for example can be designed at least substantially identical to one another. In particular, the deflection mechanism can comprise at least two and preferably several second connection members, which for example can be designed at least substantially identical to one another. The first connection members and the second connection members can be arranged alternating in series. Except at edge regions of the deflection mechanism, a connection member can be adjoined by two second connection members, or vice versa. It is moreover conceivable that at least one second connection member defines an edge region of the deflection mechanism, or two second connection members define opposite edge regions of the deflection mechanism. Here, a second connection member can be designed and/or connected at least partially integrally with an end portion of the shaft and/or the end-effector head. A first connection member is engaged, in particular from two opposite sides, by a respective second connection member. Moreover, two first connection members engage from two opposite sides in a second connection member, respectively. The first connection member and the second connection member can be connected to each other in the manner of a ball joint. In particular, the first connection member has at least one joint head, and the second connection member has at least one joint socket, which together interact in the manner of a ball joint.

The first connection member is designed as a rotation body. The first connection member has a first axis of rotational symmetry. The first connection member has in particular an olive-like shape. The second connection member is designed as a rotation body. The second connection member has a second axis of rotational symmetry. The second connection member has in particular a disk-like shape. A "straight-position spacing" should be understood in particular as a position of at least the first connection member and the second connection member, in particular of all the first and second connection members, in which the first axis of rotational symmetry and the second axis of rotational symmetry, in particular all the axes of rotational symmetry of the connection members, are oriented at least substantially parallel to one another or are even identical to one another. A "deflection position" should be understood in particular as a position of at least the first connection member and of the second connection member, in particular of all the first and second connection members, in which the first axis of rotational symmetry and the second axis of rotational symmetry, in particular all the axes of rotational symmetry of the connection members, are arranged at an angle to one another and are preferably offset relative to one another by the same angle. Being arranged "at an angle" should be understood in particular as different than being arranged at least substantially parallel.

The end effector and the actuation train can additionally be coupled electrically to each other, for example in order to transmit at least one electrical potential from the actuation train to the end effector, in particular a tool piece of the end effector. The actuation train has in particular at least one inner cable, which is preferably designed to be flexible. In particular, the inner cable can be designed to be flexible over an entire extent of the actuation train. It is conceivable that the inner cable can be designed to be electrically conductive, for example in order to transmit an electrical potential. Moreover, the actuation train can have at least one outer cable, which can advantageously be arranged coaxially surrounding the inner cable. In particular, the outer cable can be designed to be flexible over at least a large part of an extent of the actuation train. It is conceivable that the outer cable can be designed to be electrically conductive, for example in order to transmit a further electrical potential. The outer cable could be designed as a hose. For example, the outer cable could be designed as a woven fabric.

The control train of the deflection mechanism is in particular designed to be flexurally slack. A "flexurally slack component" should be understood in particular as a component, preferably an elongate component, which has flexurally slack properties at least in one direction perpendicular to a direction of principal extent. It should preferably be understood in particular as a dimensionally non-stable component. Particularly preferably, it should be understood in particular as a component which, in an elongated state of a pressure force acting parallel to a direction of principal extent, exerts a counterforce which is less than a weight force of the component. Preferably, the counterforce is at most 70%, preferably at most 50% and particularly preferably at most 30% of a weight force. Here, an "elongate component" should be understood in particular as a component having a transverse extent that is many times smaller than a longitudinal extent. Here, "many times smaller" should be understood in particular as at least 3 times smaller, preferably at least 5 times smaller and particularly preferably at least 10 times smaller.

It is proposed that a spacing between the geometric midpoints of the connection members increases at least by 0.3 μm per degree of a deflection of these from the straight position. Bracing of the connection members relative to each other during a deflection can advantageously be increased, as a result of which it is possible to achieve a self-resetting, which can return the connection members to the straight position. Moreover, a degree of self-resetting can advantageously be adjusted depending on an increase in the spacing. A totality of the connection members of the deflection mechanism results, during a deflection of these from the straight position, in an increase in all the spacings relative to each other by at least 1.8 μm per degree of a deflection. For example, during a deflection by at least 90°, there is thus an increase in all the spacings relative to each other by at least 162 μm. Moreover, particularly with a deflection of at least 90°, an angle of at least 15° arises between a first connection member and a second connection member.

In one aspect of the invention, which can be considered in particular in combination with further aspects of the invention, it is proposed that the first connection member has at least one outer contour and the second connection member has at least one inner contour interacting with the outer contour of the first connection member, wherein the inner contour and/or the outer contour are/is other than concave.

In this way, an endoscopic device can advantageously be equipped with a resetting function. It is advantageously possible to avoid a situation where connection members of the deflection mechanism are oriented randomly relative to each other upon a return of the deflectable portion from a basic deflection position.

An "outer contour" is to be understood in particular as an outwardly directed contour. An "inner contour" is to be understood in particular as an inwardly directed contour. The outer contour and the inner contour bear in particular on each other. It is conceivable that either only the inner contour or the outer contour has a shape other than concave. However, it is preferable that both the inner contour and the outer contour have a shape other than concave. In particular, the inner contour and the outer contour are not shaped corresponding to each other.

It is proposed that the outer contour and the inner contour bear on each other at most in part. A rolling of the connection members on each other can advantageously be improved, since they do not bear on each other over a large surface area, and therefore a frictional resistance can be reduced.

It is further proposed that the outer contour and/or the inner contour are convex. A rolling of the connection members on each other can advantageously be further improved, since they do not bear on each other over a large surface area, and therefore a frictional resistance can be reduced. In particular, the outer contour and the inner contour can be convex. Moreover, either the outer contour or the inner contour could be convex. It is moreover conceivable that the outer contour and/or the inner contour are/is neither convex nor concave. For example, the outer contour and/or the inner contour could be straight. Preferably, the outer contour can be convex and the inner contour straight.

It is further proposed that a diameter of a smallest arc of a circle still completely enclosing the outer contour is greater than a connection member width of the first connection member measured perpendicularly to a direction of longitudinal extent of the shaft. A self-resetting can advantageously be further improved. Moreover, a degree of self-resetting, i.e. in particular a spacing between the geometric midpoints of the connection members, can advantageously be adjusted depending on a ratio of the diameter and of the width. In other words, a midpoint of the smallest arc of a circle that encloses the outer contour lies in particular to the other side of a geometric midpoint of the connection member.

It is further proposed that the outer contour and/or the inner contour are/is different at least in part from an arc of a circle. Rolling of the connection members on each other can advantageously be further improved. Moreover, a self-aligning or self-locking action of the connection members can advantageously be further improved. In particular, either the outer contour or the inner contour could be, at least in part, different from an arc of a circle. It is moreover conceivable that the outer contour and the inner contour are, at least in part, different from an arc of a circle.

It is moreover proposed that the outer contour and/or the inner contour are/is designed corresponding at least in part to a shape of an arc of a circle, a circle involute, a cycloid, a paraboloid and/or an ellipsoid. Rolling of the connection members on each other can advantageously be further improved. Moreover, a self-aligning or self-locking action of the connection members can advantageously be further improved. In particular, either the outer contour or the inner contour could be designed corresponding at least in part to a shape of an arc of a circle, a circle involute, a cycloid, a paraboloid and/or an ellipsoid. It is moreover conceivable that the outer contour and the inner contour are designed corresponding at least in part to a shape of an arc of a circle, a circle involute, a cycloid, a paraboloid and/or an ellipsoid.

It is further proposed that the endoscopic device has at least one flexurally slack control train on which the connection members are arranged in rows and which, in the straight position of the connection members, keeps the connection members pretensioned. A deflection of the connection members can advantageously be improved.

It is proposed that the deflection mechanism has a number of first connection members and a number of second connection members, wherein a difference between the number of the first connection members and the number of the second connection members is different than zero. A self-resetting can advantageously be further improved. Moreover, a degree of self-resetting, in particular a spacing between the geometric midpoints of the connection members, can advantageously be adjusted depending on a number of the connection members. Preferably, the deflection mechanism has an odd number of first connection members. In the present case, the deflection mechanism can have three first connection members, Preferably, the deflection mechanism has an even number of second connection members. In the present case, the deflection mechanism can have four second connection members.

The subject matter of the present disclosure is not intended to be restricted to the usage and embodiment described above. In particular, the subject matter of the present disclosure may, in order to realize a functionality described herein, have a number of individual elements, components and units, and also method steps, which differs from a number stated herein. Moreover, in the case of the value ranges specified in this disclosure, values lying within the stated limits are also intended to be disclosed and usable as desired.

If there is more than one instance of a specific object, only one of them is provided with a reference sign in the figures and in the description. The description of this instance can accordingly be transferred to other instances of the object.

DRAWINGS

Further advantages will become clear from the following description of the drawings. The drawings illustrate exemplary embodiments of the disclosure. The drawings, the description and the claims contain numerous features in combination. A person skilled in the art will expediently also consider the features individually and combine them to form meaningful further combinations.

Figure 2:
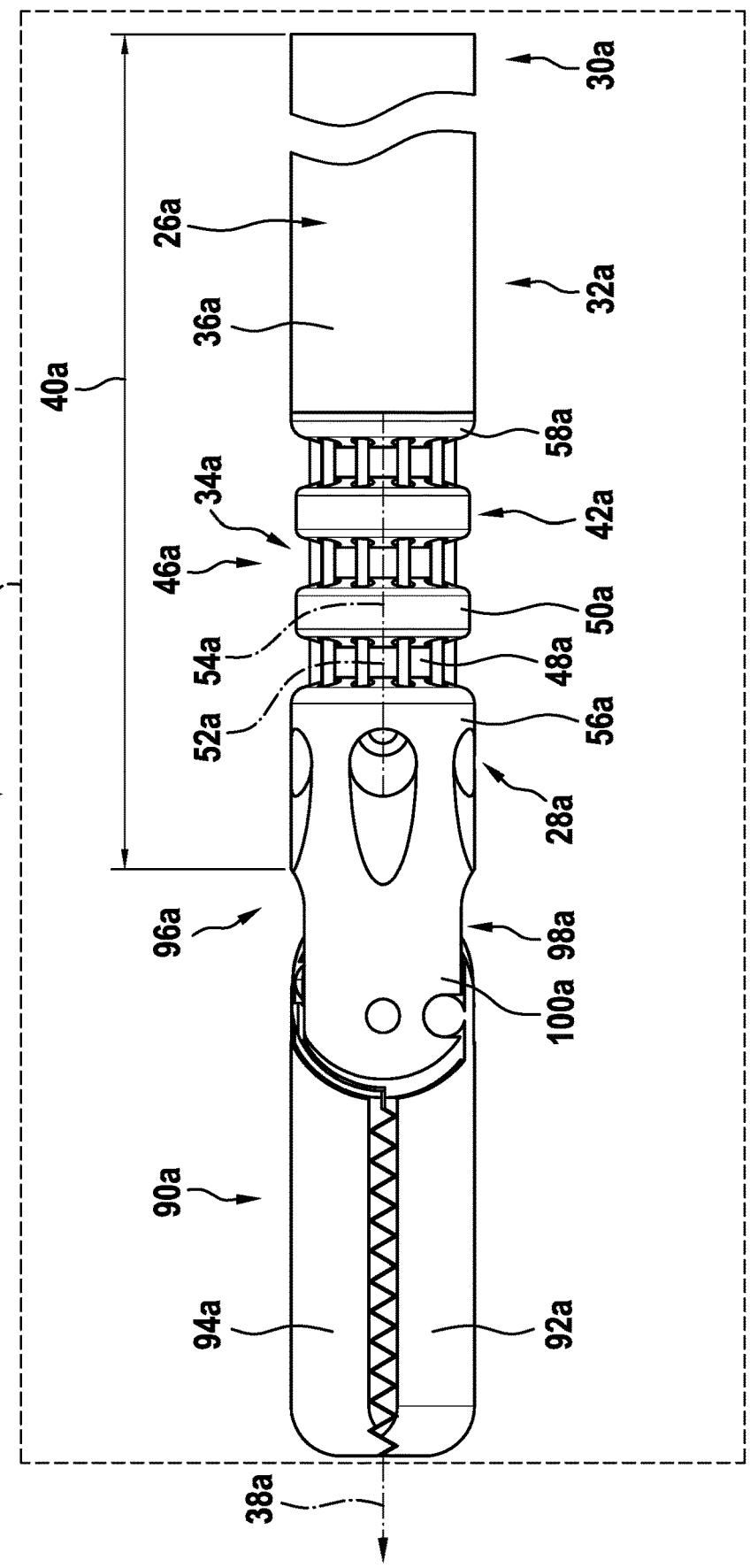
Figure 3:
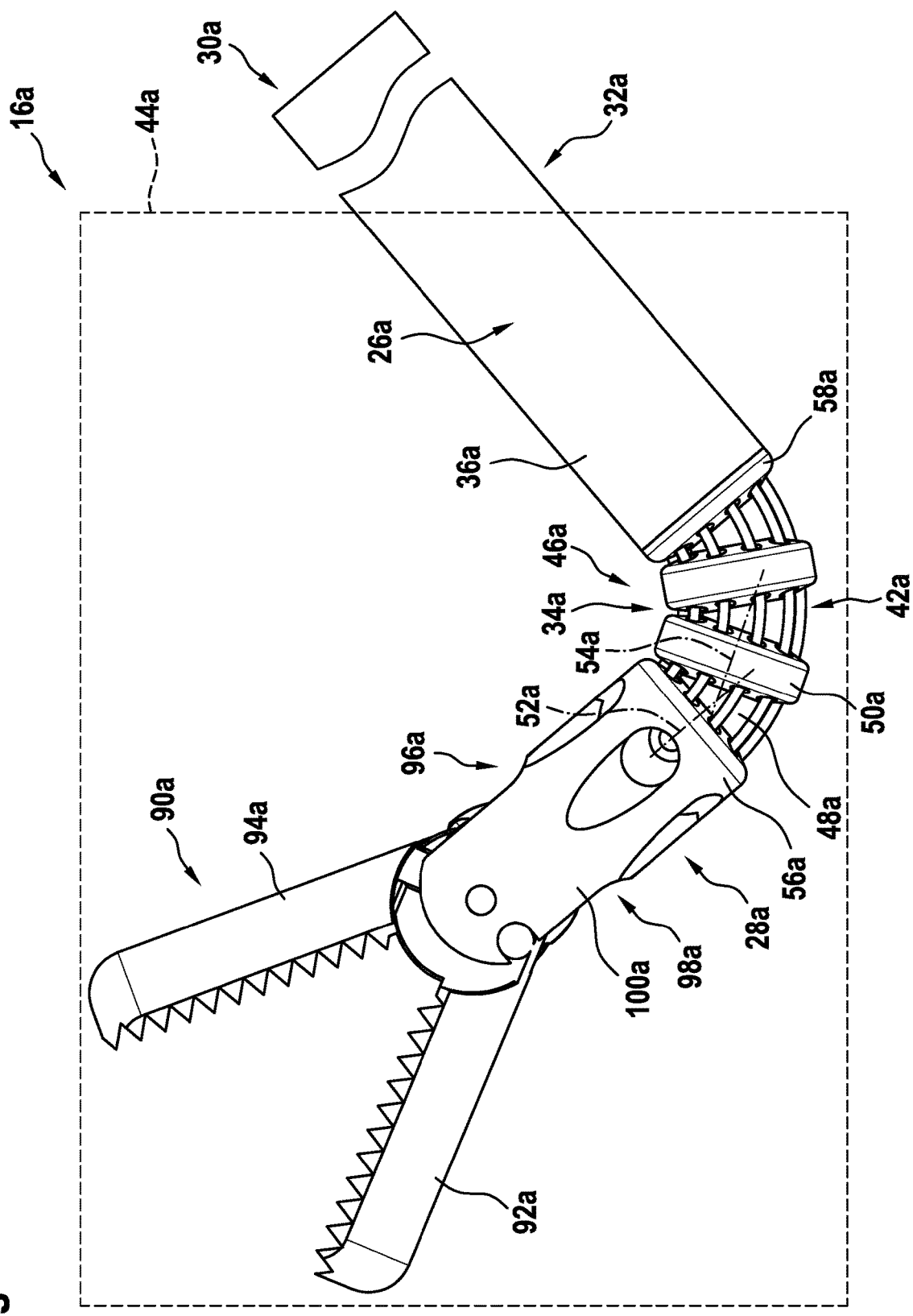
Figure 4:
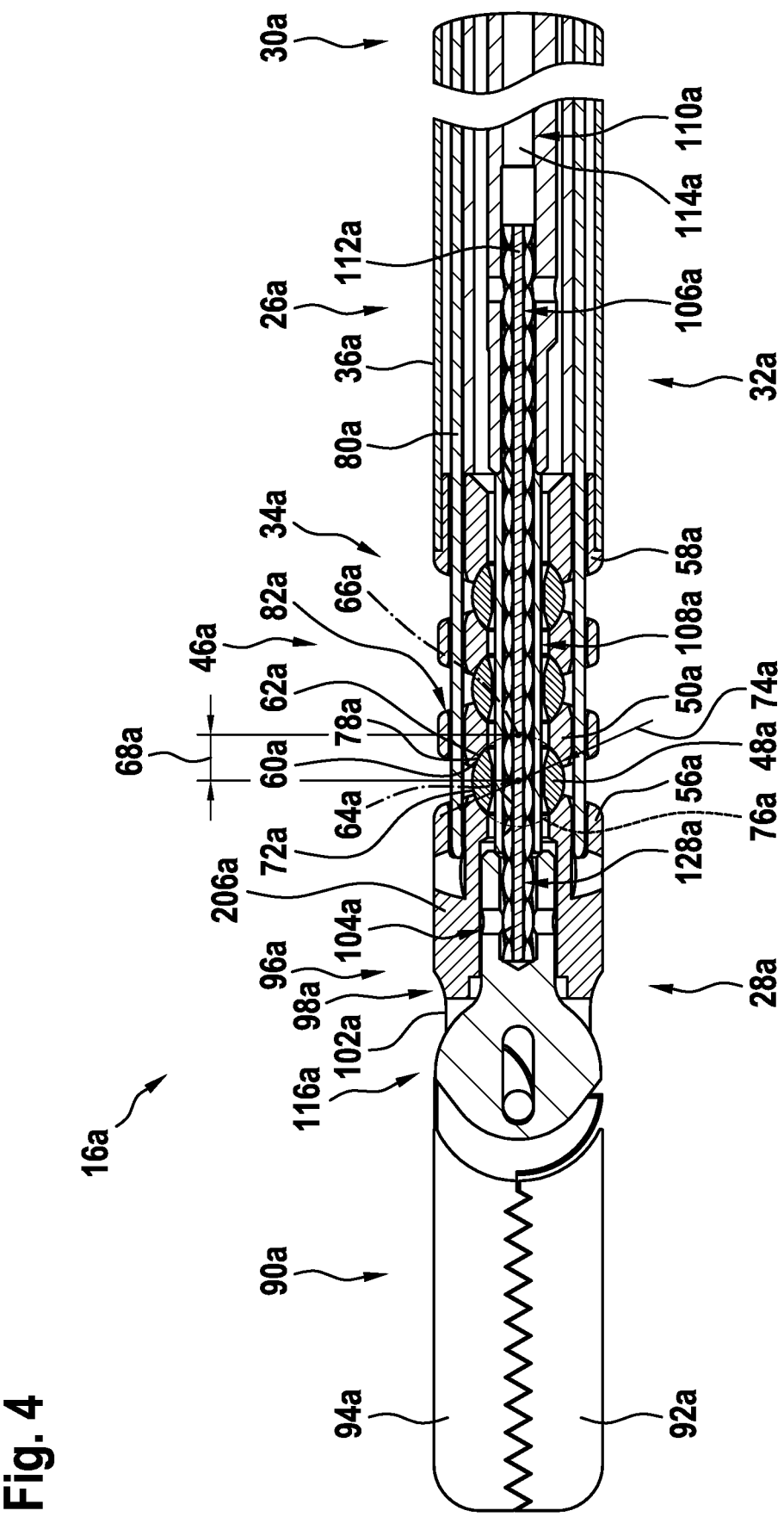
Figure 5:
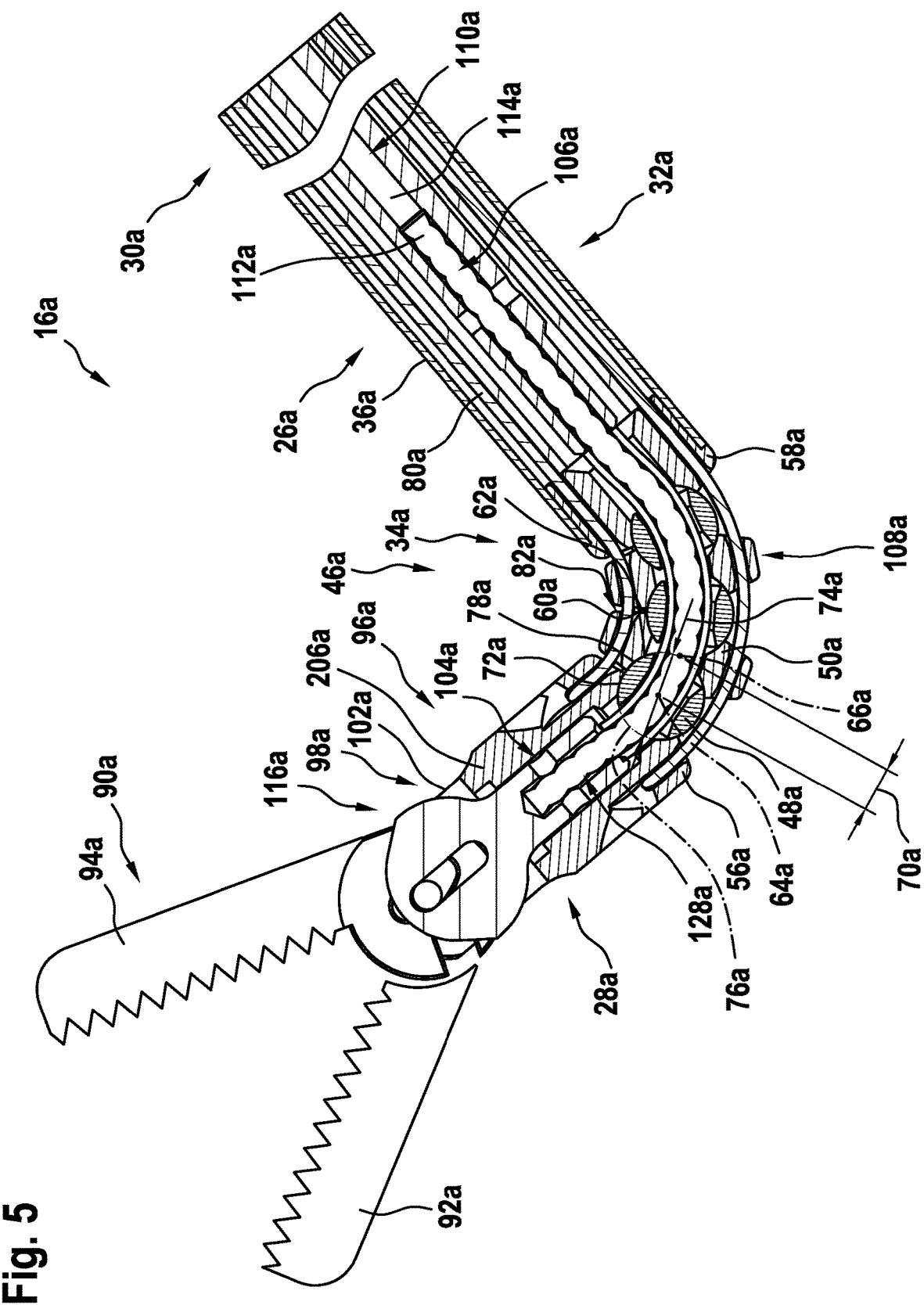
Figure 6:
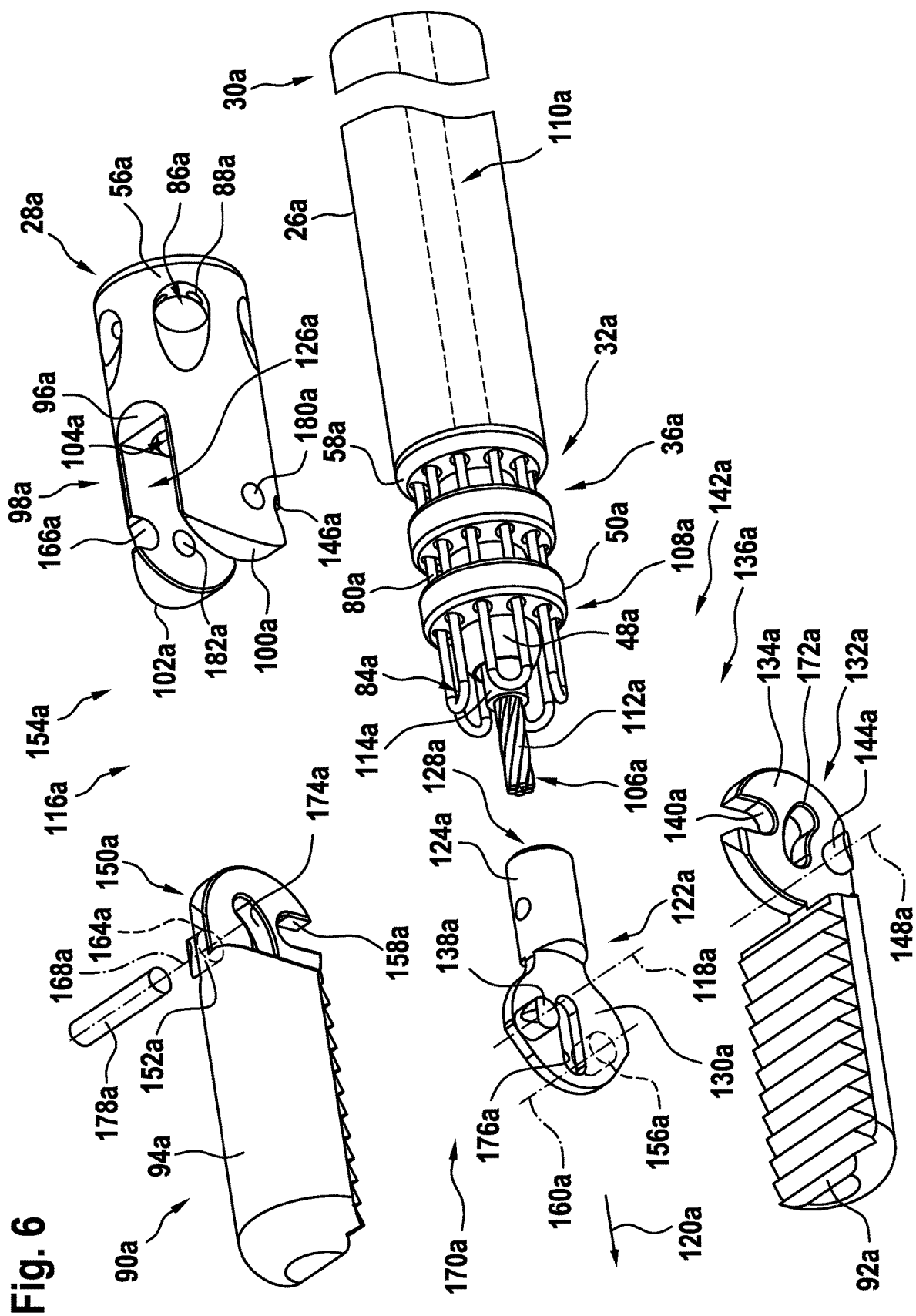
Figure 7:
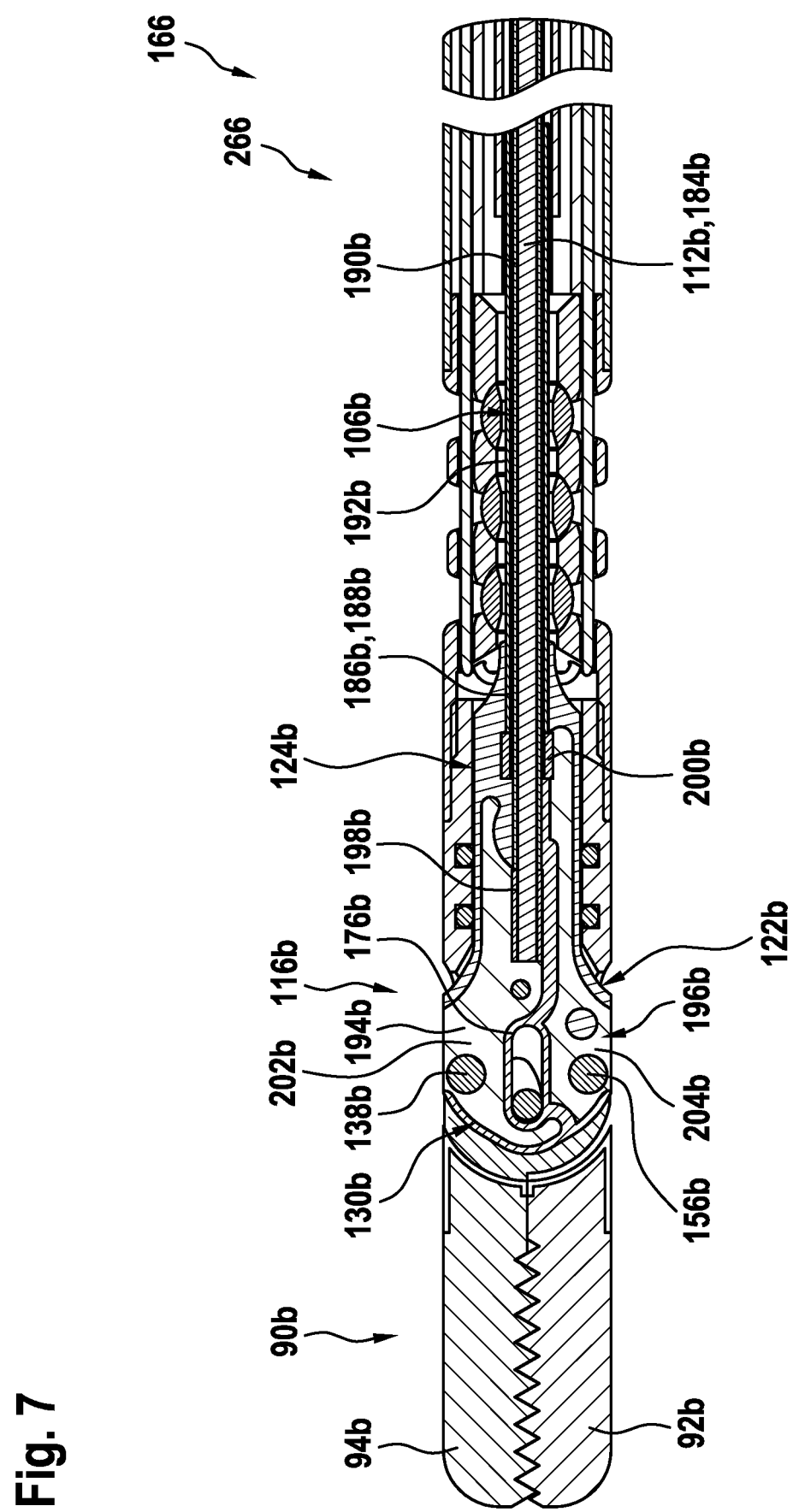
Figure 8:
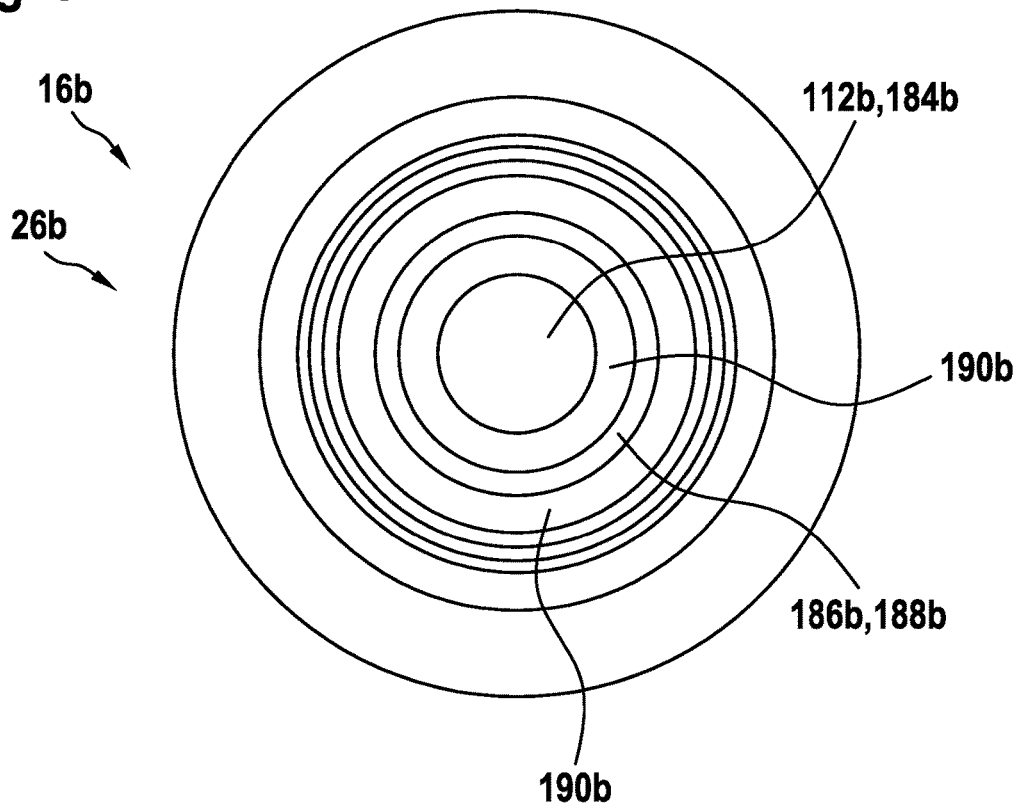
Figure 9:
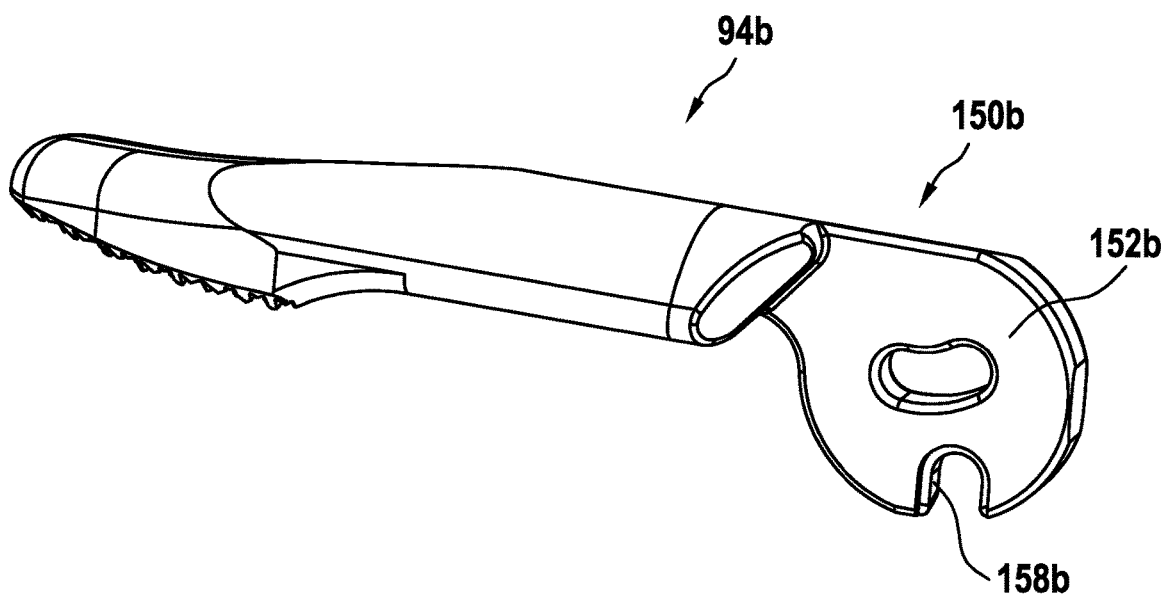
Figure 10:
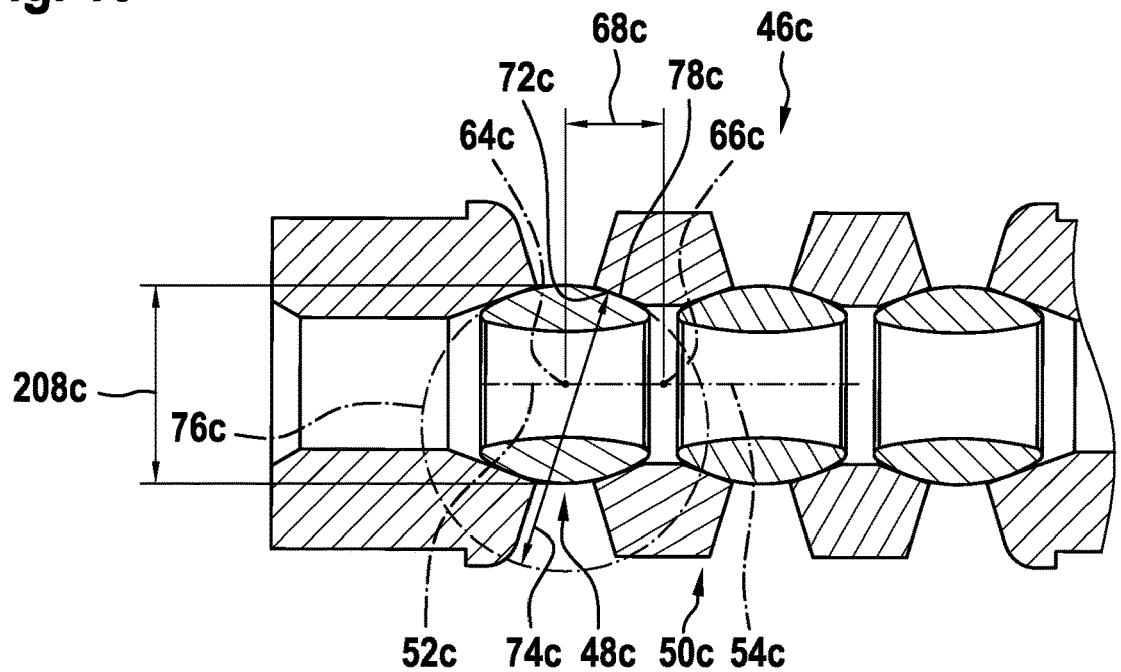
Figure 11:
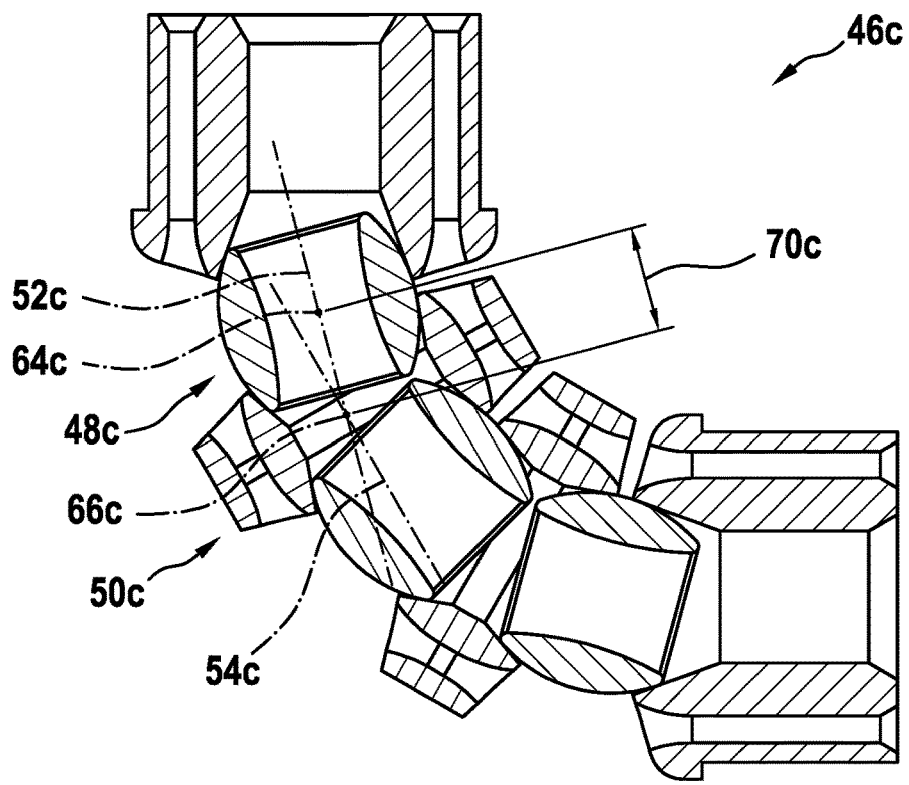
Figure 12:
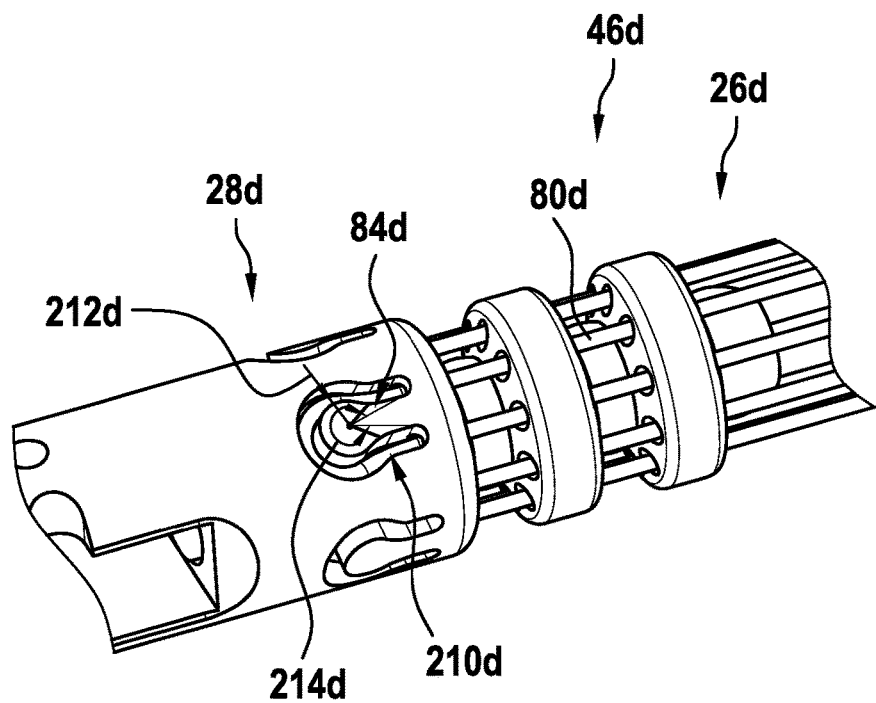
Figure 13:
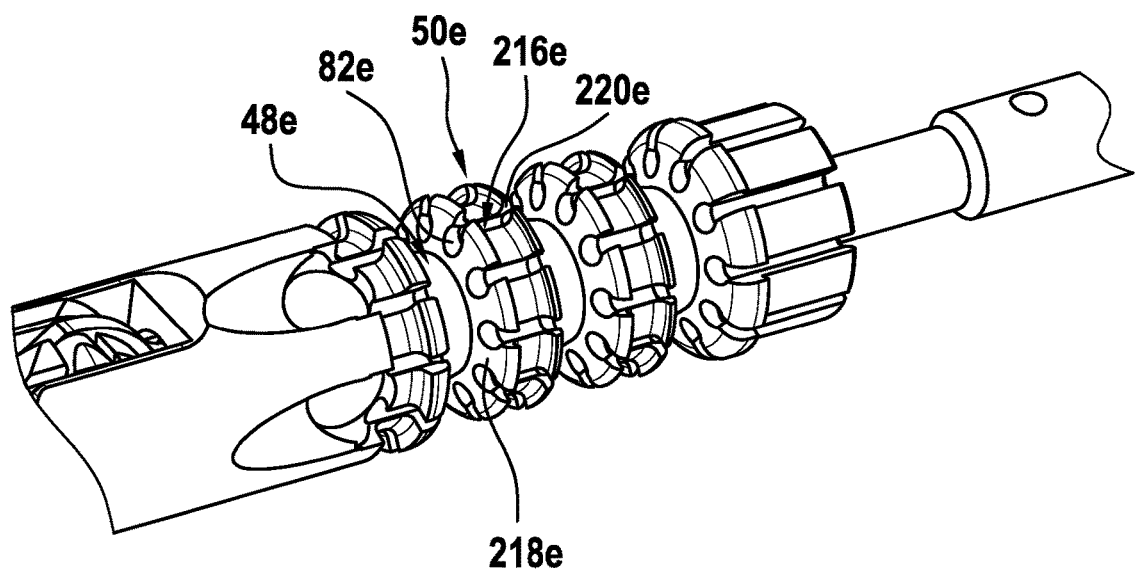
Figure 14:
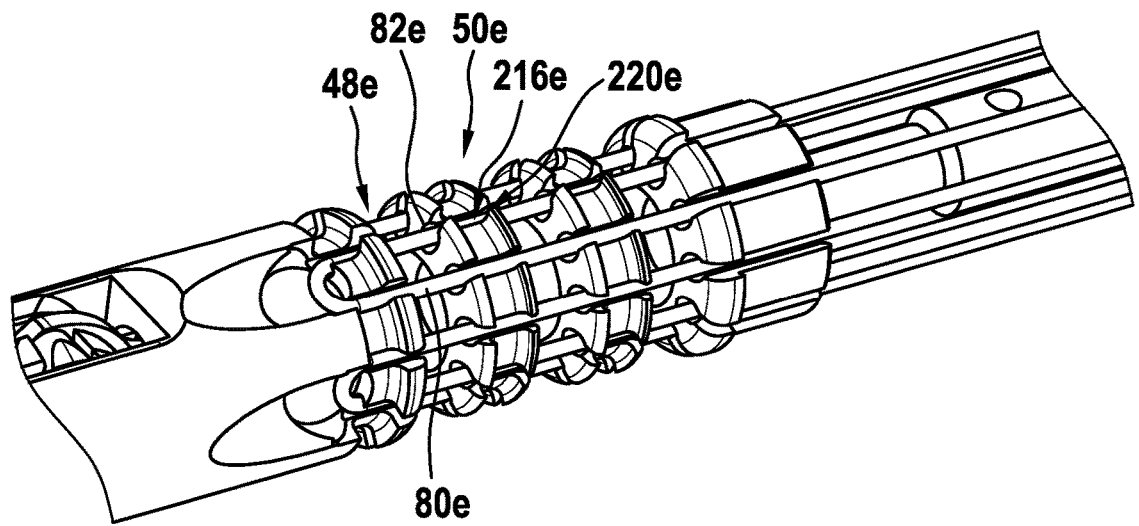
Figure 15:
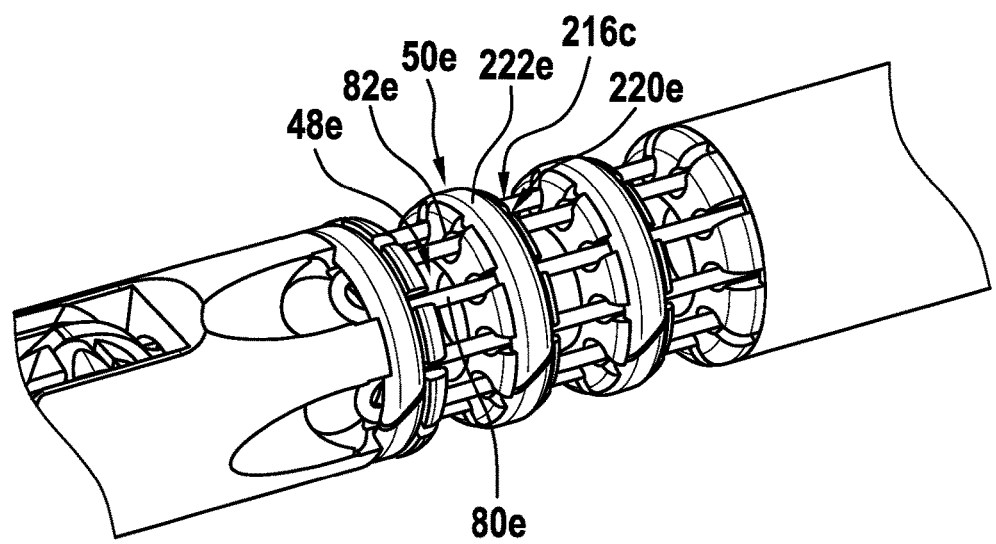
Figure 16:
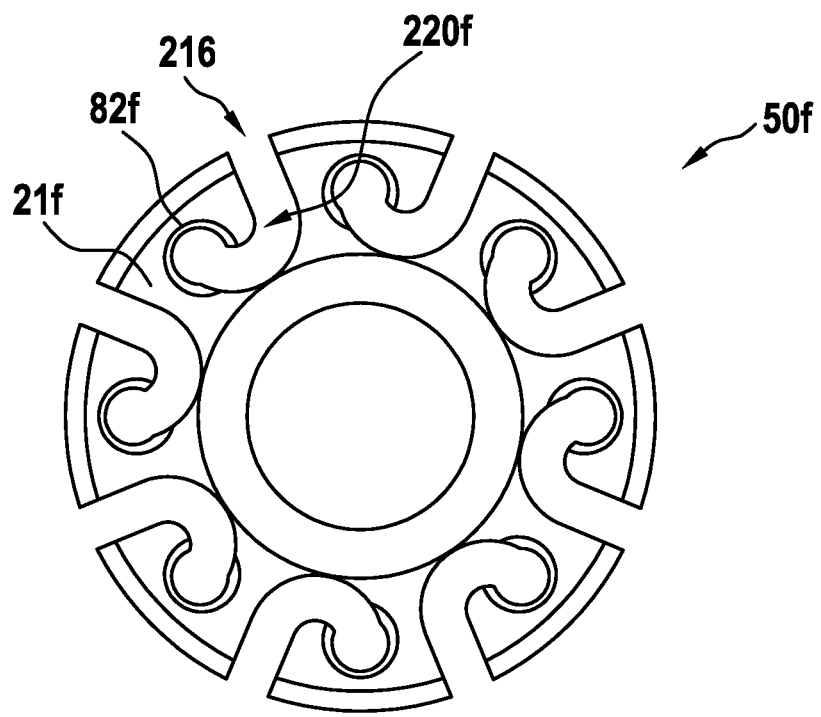
Figure 17:
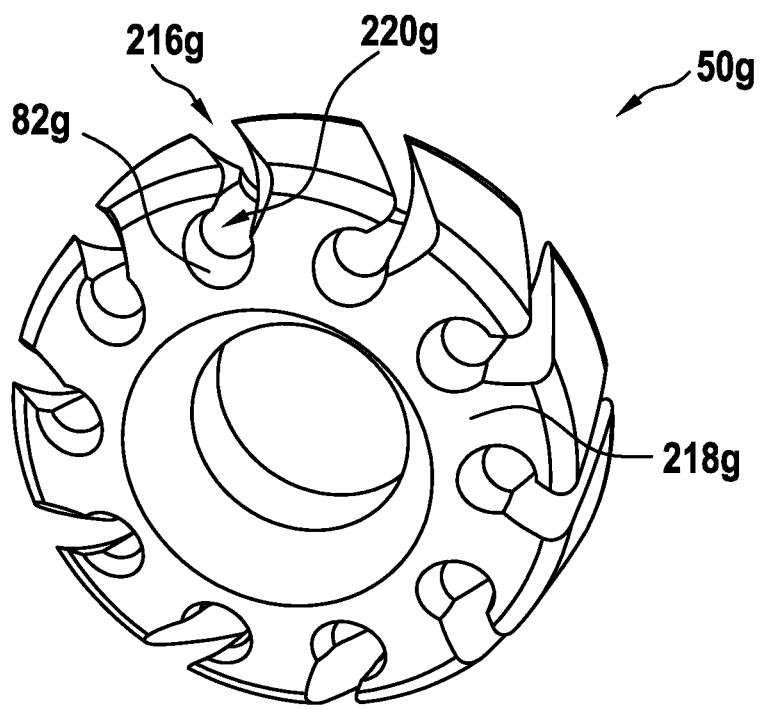
Figure 18:
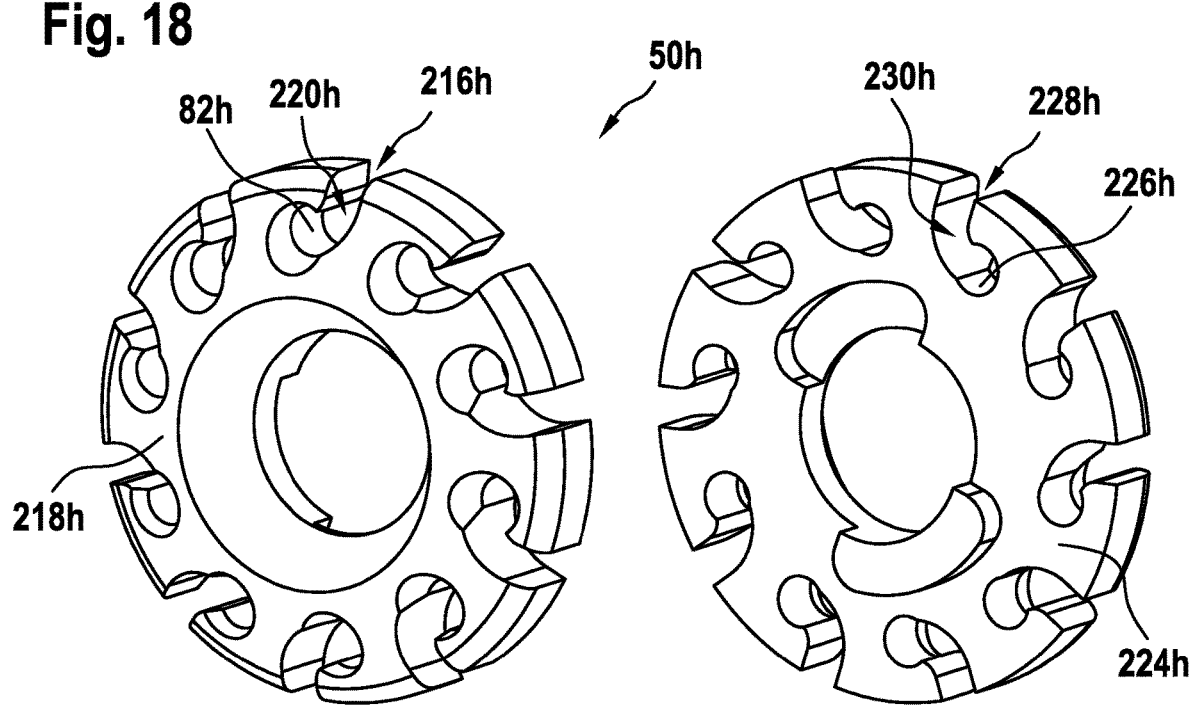
Figure 19:
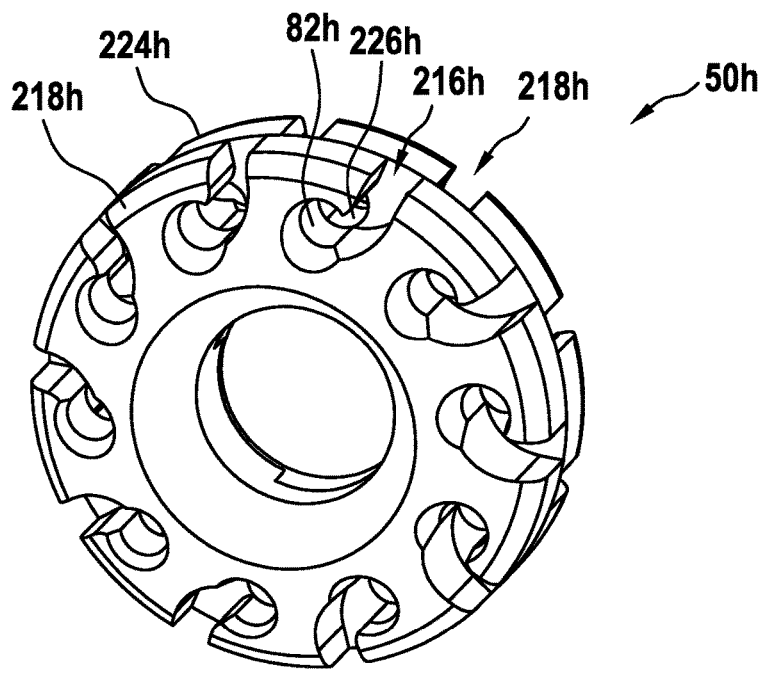
Figure 20:
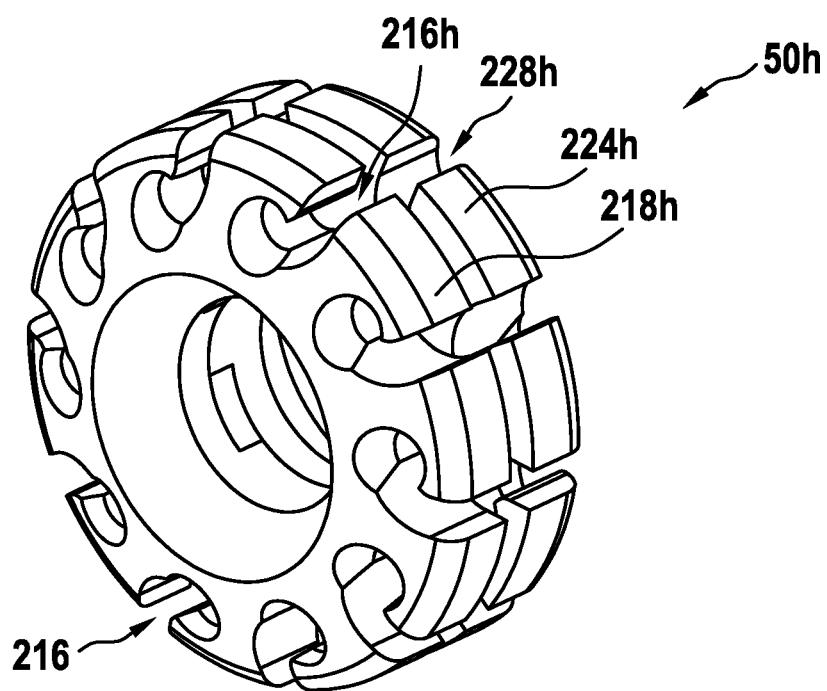
Figure 21:
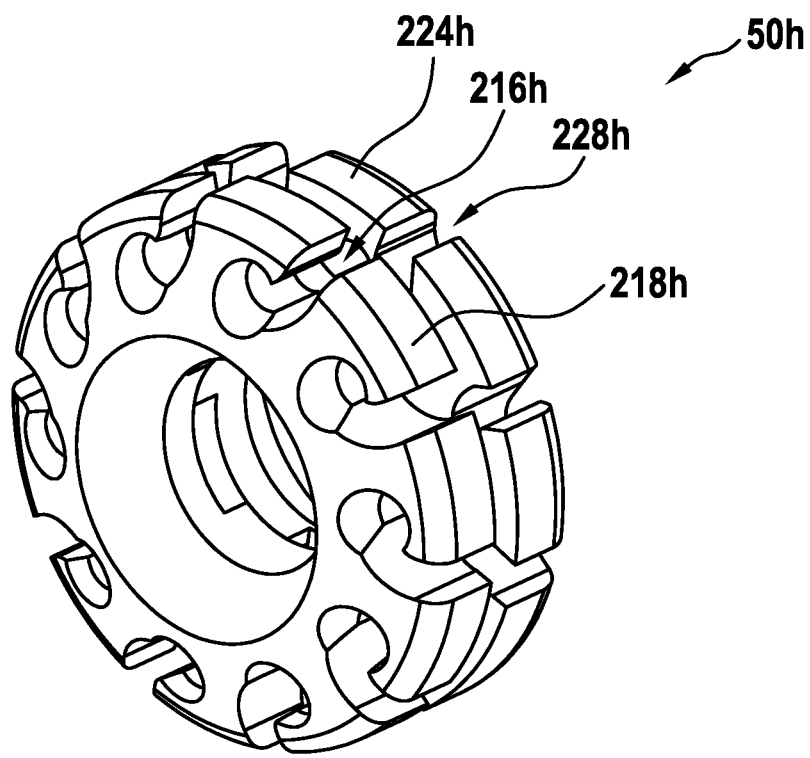
Figure 22:
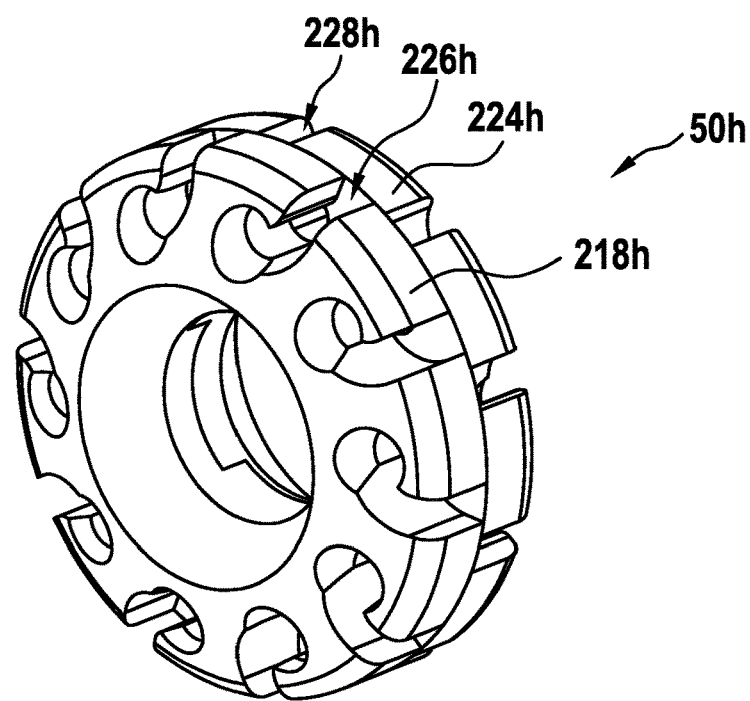
Figure 23:
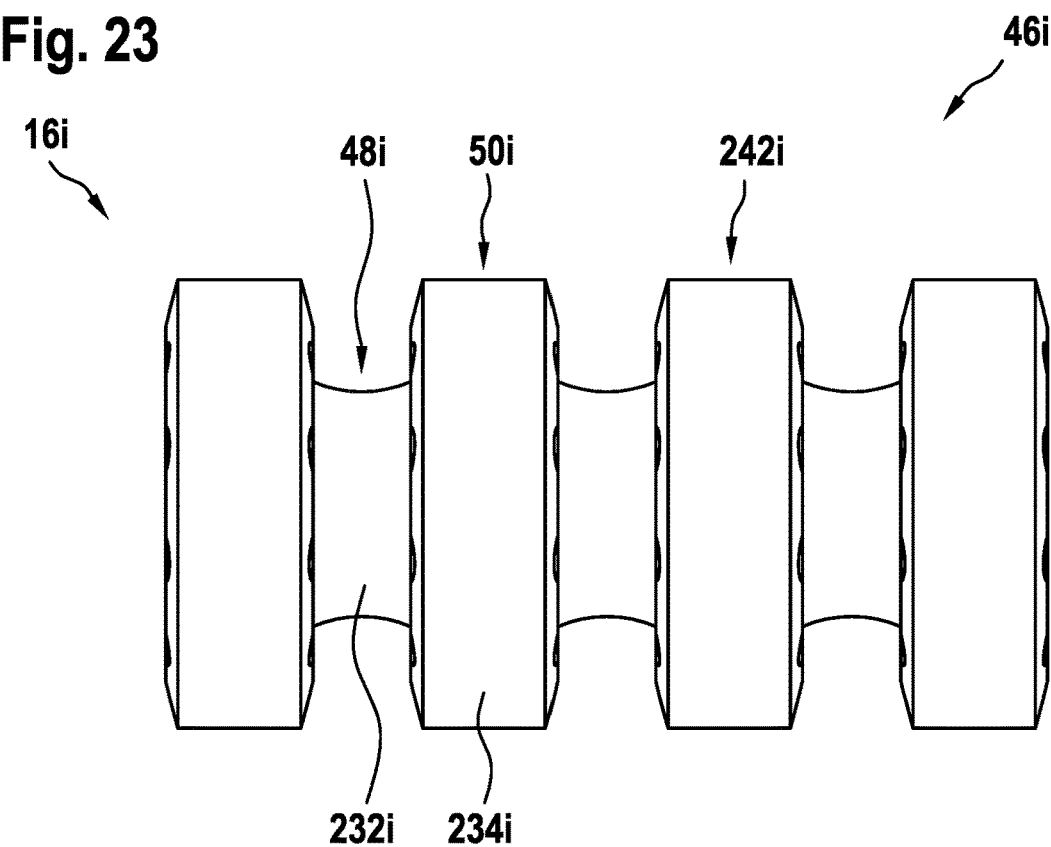
Figure 24:
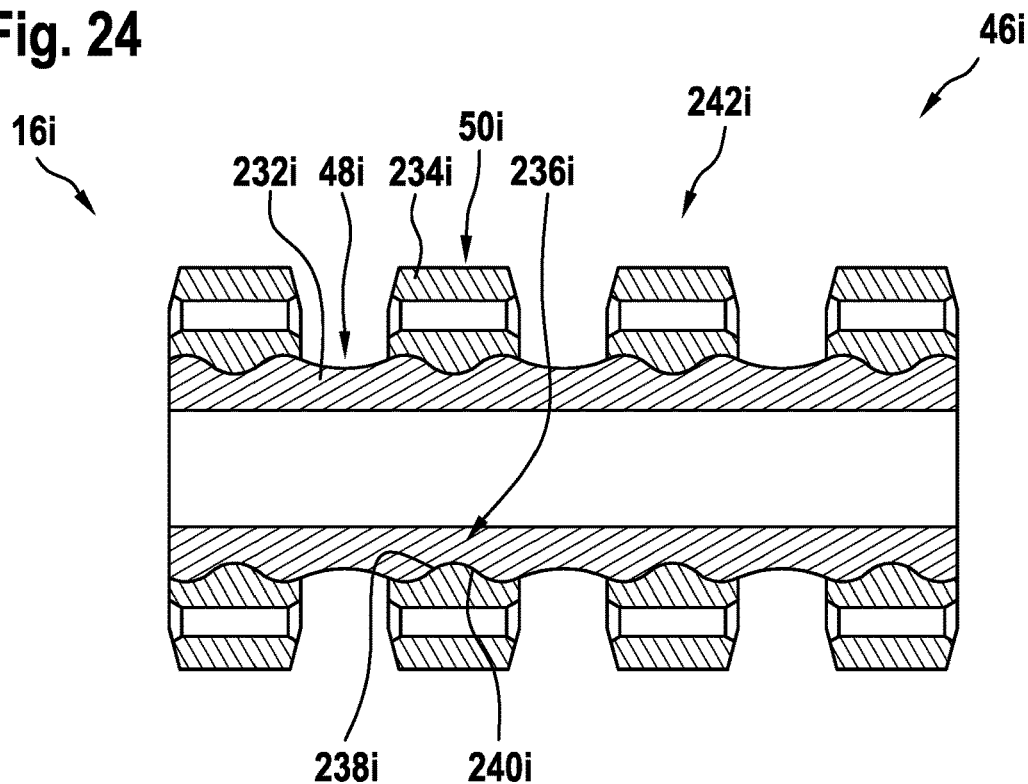
Figure 25:
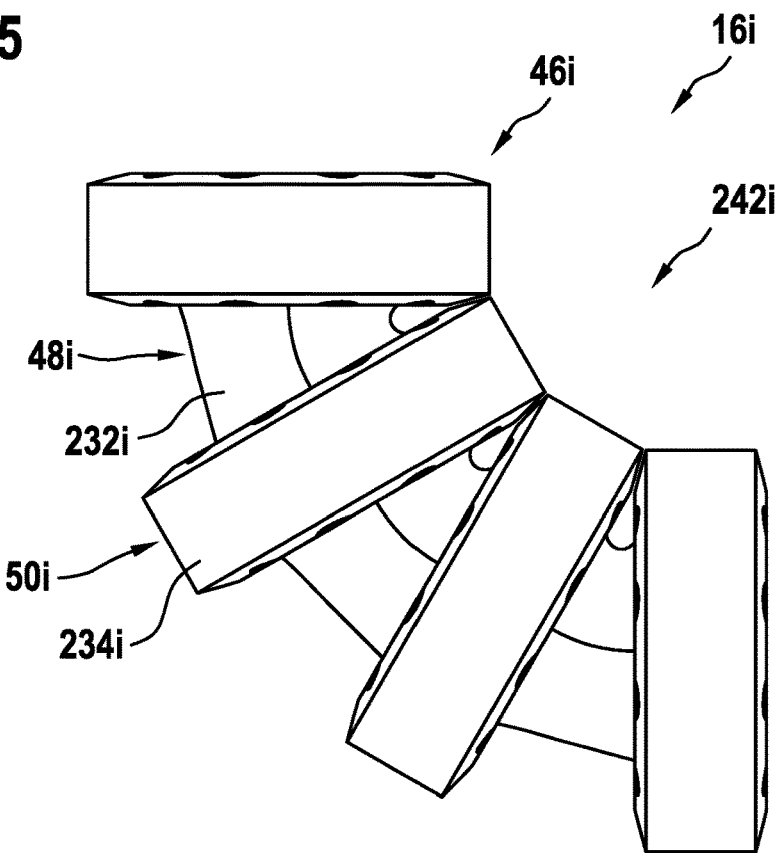
Figure 26:
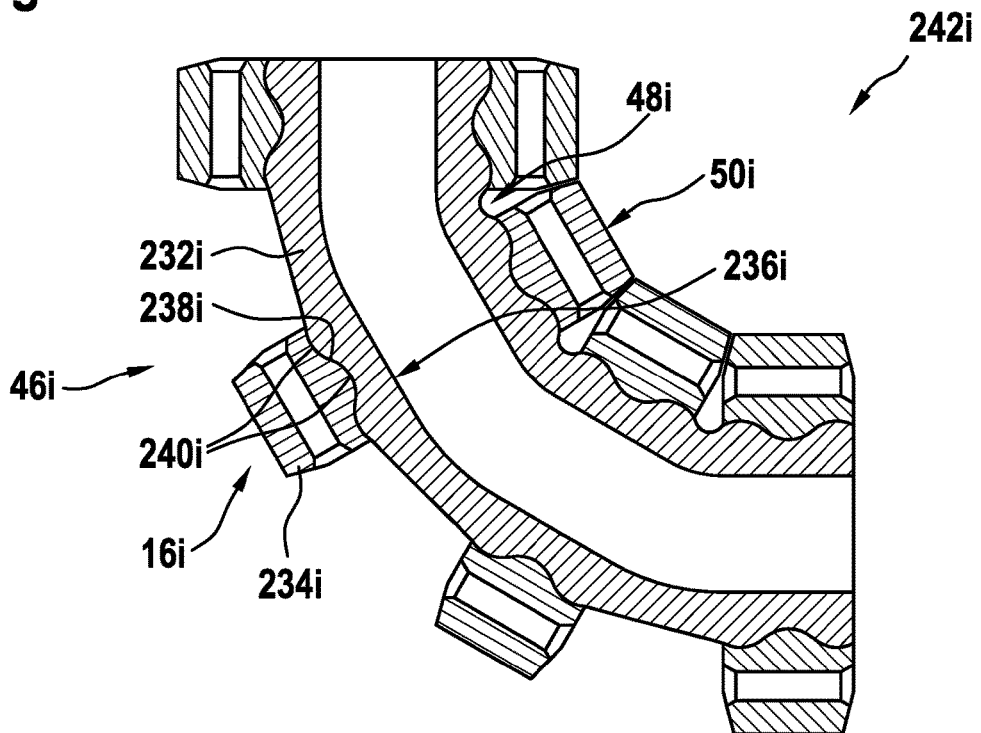
Figure 27:
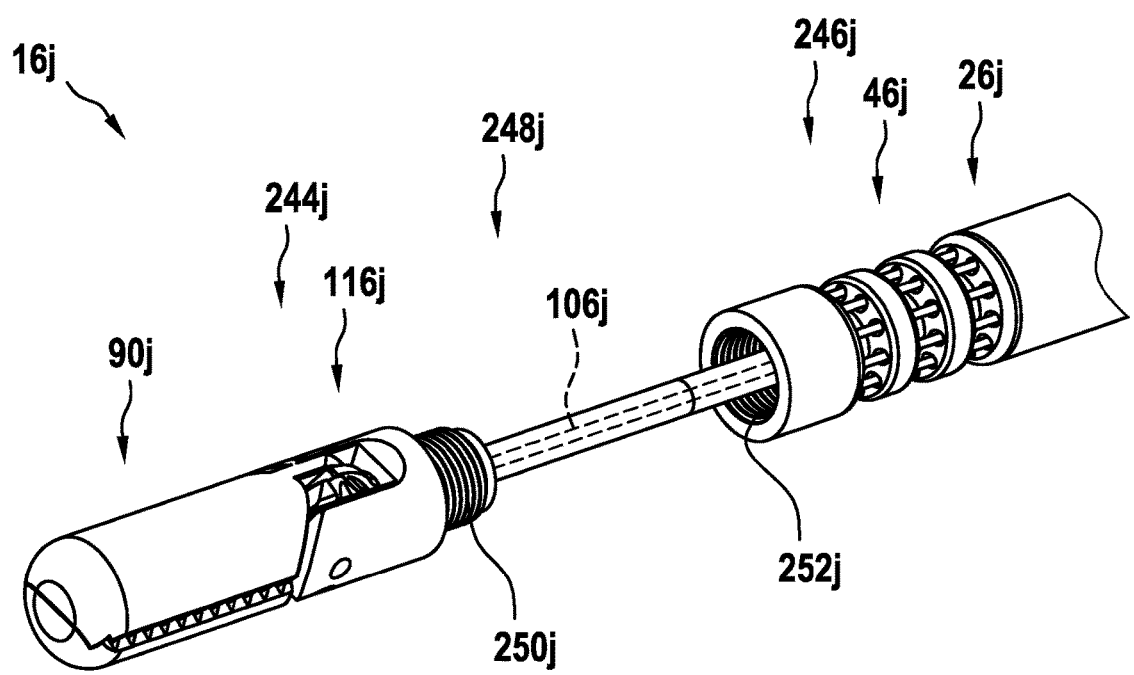

In the drawings:

FIG. 1 shows a schematic perspective view of a surgical system having an endoscopic device, FIG. 2 shows a schematic side view of a part of the endoscopic device located in a straight position, FIG. 3 shows a schematic side view of a part of the endoscopic device located in a deflection position, FIG. 4 shows a schematic sectional view of a part of the endoscopic device located in a straight position, FIG. 5 shows a schematic sectional view of a part of the endoscopic device located in a deflection position, FIG. 6 shows a schematic perspective view of a part of the endoscopic device located in a partially dismantled state, FIG. 7 shows schematically at least one part of a further endoscopic device, in a sectional view along a shaft of the endoscopic device, FIG. 8 shows schematically at least one part of the endoscopic device from FIG. 7, in a sectional view transverse to a shaft of the endoscopic device, FIG. 9 shows a schematic perspective view of a part of the endoscopic device from FIG. 7, FIG. 10 shows schematically at least one part of an alternative endoscopic device, in a sectional view along a shaft of the endoscopic device in a straight position, FIG. 11 shows schematically at least one part of the endoscopic device from FIG. 10, in a sectional view along the shaft of the endoscopic device in a deflection position, FIG. 12 shows a schematic perspective view of at least one part of a further endoscopic device, FIG. 13 shows a schematic perspective view of at least one part of an additional endoscopic device, in an assembly state, FIG. 14 shows a schematic perspective view of at least one part of the endoscopic device from FIG. 13, in a further assembly state, FIG. 15 shows a schematic perspective view of at least one part of the endoscopic device from FIG. 13 and FIG. 14, in an additional assembly state, FIG. 16 shows a schematic plan view of at least one part of a further endoscopic device, FIG. 17 shows a schematic perspective view of at least one part of an alternative endoscopic device, FIG. 18 shows a schematic perspective view of at least one part of an alternative endoscopic device, in an assembly state, FIG. 19 shows a schematic perspective view of at least one part of the endoscopic device from FIG. 18, in a mounted state, FIG. 20 shows a schematic perspective view of at least one part of the endoscopic device from FIG. 18, in an assembly state, FIG. 21 shows a schematic perspective view of at least one part of the endoscopic device from FIG. 18, in a further assembly state, FIG. 22 shows a schematic perspective view of at least one part of the endoscopic device from FIG. 18, in a mounted state, FIG. 23 shows a schematic side view of at least one part of an alternative endoscopic device in a straight position, FIG. 24 shows schematically at least one part of the endoscopic device from FIG. 23, in a sectional view along a shaft of the endoscopic device in the straight position, FIG. 25 shows a schematic side view of at least one part of the endoscopic device from FIGS. 23 and 24, in a deflection position, FIG. 26 shows schematically at least one part of the endoscopic device from FIGS. 23,24 and 25, in a sectional view along the shaft of the endoscopic device in the deflection position, FIG. 27 shows a schematic perspective view of at least one part of an alternative endoscopic device, in an assembly state.

DESCRIPTION OF THE EXEMPLARY EMBODIMENTS

FIG. 1 shows a schematic perspective view of a surgical system 10a. The surgical system 10a comprises at least one surgical robot 12a. The surgical system 10a moreover comprises at least one controller 14a. The controller 14a is configured to control the surgical robot 12a.

The surgical robot 12a is configured to guide at least one endoscopic device 16a of the surgical system 10a. For this purpose, the surgical robot 12a has at least one robot arm 18a. In an operating state, the endoscopic device 16a is coupled to the robot arm 18a. The endoscopic device 16a can be connected releasably to the robot arm 18a, for example in order to exchange it, modify it, sterilize it or the like. In the present case, the surgical robot 12a has a plurality of robot arms. Of said robot arms, for the sake of clarity only the robot arm 18a is provided with a reference sign.

The surgical system 10a comprises at least one endoscopic device 16a. In the present case, the surgical system 10a comprises a plurality of endoscopic devices. The surgical robot 12a has one robot arm 18a per endoscopic device 16a. Of said endoscopic devices, for the sake of clarity only the endoscopic device 16a is provided with a reference sign. The plurality of endoscopic devices could be designed substantially identical to one another. Substantially identical can mean except for production and/or assembly tolerances. However, it is conceivable that the plurality of endoscopic devices could be designed to be at least partially different from one another and, for example, could differ from one another in terms of an end effector and/or a mode of function. Moreover, it would be obvious for a person skilled in the art to adapt the plurality of endoscopic devices for different surgical uses according to his knowledge in the art.

The endoscopic device 16a at least partially forms an endoscopic instrument 20a. In the present case, the endoscopic device 16a completely forms an endoscopic instrument 20a. However, an endoscopic device could only be a constituent part of an endoscopic instrument. Moreover, an endoscopic device, for example one of the plurality of endoscopic devices, could at least partially or completely form an endoscope 22a. However, an endoscopic device could also only be a constituent part of an endoscope.

FIG. 2 shows a schematic side view of a part of the endoscopic device 16a located in a straight position. Moreover, FIG. 3 shows a schematic side view of a part of the endoscopic device 16a located in a deflection position.

The endoscopic device 16a has at least one shaft 26a. In the present case, the endoscopic device 16a has precisely one shaft 26a. The shaft 26a has a direction of longitudinal extent 38a. The direction of longitudinal extent 38a corresponds to a direction of principal extent of the shaft 26a in the straight position. A longitudinal extent 40a of the shaft 26a extends along the direction of longitudinal extent 38a of the shaft 26a.

The shaft 26a comprises at least one end portion 28a. The end portion 28a is a distal end portion. The end portion 28a is configured for the treatment of a patient. Moreover, the shaft 26a has a further end portion 30a. The further end portion 30a is a proximal end portion. The further end portion 30a is configured for coupling to the surgical robot 12a, for example to the robot arm 18a thereof. The end portion 28a and the further end portion 30a lie opposite each other. Moreover, the shaft 26a has a middle portion 32a. The middle portion 32a connects the end portion 28a and the further end portion 30a to each other. The middle portion 32a is arranged between the end portion 28a and the further end portion 30a.

The shaft 26a has a main framework 34a. The main framework 34a extends from the end portion 28a to the further end portion 30a of the shaft 26a. Moreover, the shaft 26a has a shaft jacket 36a. The shaft jacket 36a at least partially surrounds the main framework 34a. In the present case, the shaft jacket 36a at least largely surrounds the main framework 34a. The shaft jacket 36a is arranged coaxially to the main framework 34a. The shaft jacket 36a at least partially surrounds the middle portion 32a. In the present case, the shaft jacket 36a at least largely surrounds the middle portion 32a. Moreover, the shaft 26a can have a shaft casing. For the sake of clarity, a shaft casing is not shown in the figures, so as to be able to better show the structure of the main framework 34a. A shaft casing can be configured to seal off the shaft 26a from the outside.

The shaft 26a has at least one deflectable portion 42a. The deflectable portion 42a is arranged between the end portion 28a and the further end portion 30a. The deflectable portion 42a is part of the middle portion 32a. The deflectable portion 42a directly adjoins the end portion 28a. The deflectable portion 42a is spaced apart from the further end portion 30a. Alternatively, it is conceivable that a deflectable portion at least partially forms an end portion, for example a distal end portion. Advantageously, the deflectable portion could be surrounded by a shaft casing. The shaft casing can be at least partially elastic and/or flexible. For example, the shaft casing can be a rubber hose.

The deflectable portion 42a is deflectable in at least one plane 44a. In FIG. 2, the plane 44a corresponds to an image plane of the figure. In the present case, the deflectable portion 42a is even deflectable in a plurality of planes, of which, for the sake of clarity, only the plane 44a is provided with a reference sign and shown in the figures. In the present case, the deflectable portion 42a is even deflectable along a full circumference of the shaft 26a. The deflectable portion 42a is designed to be at least partially flexible.

The main framework 34a of the shaft 26a has a cuff 56a. The cuff 56a at least partially forms the end portion 28a of the shaft 26a. The cuff 56a adjoins the deflectable portion 42a at the distal end. Moreover, the main framework 34a of the shaft 26a has a further cuff 58a. The further cuff 58a at least partially forms the middle portion 32a of the shaft 26a. The further cuff 58a adjoins the deflectable portion 42a at the proximal end.

The endoscopic device 16a has at least one deflection mechanism 46a. The deflection mechanism 46a is configured for the deflection of the deflectable portion 42a of the shaft 26a. In the region of the deflectable portion 42a, the deflection mechanism 46a at least partially forms the main framework 34a of the shaft 26a.

The deflection mechanism 46a has at least one first connection member 48a. In the present case, the deflection mechanism 46a has a plurality of first connection members, for example three first connection members. Of the plurality of first connection members, for the sake of clarity only the first connection member 48a is provided with a reference sign. The plurality of first connection members are designed substantially identical. A description of the first connection member 48a can be applied to the plurality of first connection members. Alternatively, however, the plurality of first connection members could also be designed differing at least partially from one another.

The first connection member 48a is symmetrical. The first connection member 48a is designed substantially as a rotation body. The first connection member 48a has a first axis of rotational symmetry 52a. About the first axis of rotational symmetry 52a, the first connection member 48a has at least one two-fold rotational symmetry. For example, a number of a first rotational symmetry could correspond to a number of planes in which the deflectable portion is deflectable. In a straight position, the direction of longitudinal extent 38a of the shaft 26a corresponds to the first axis of rotational symmetry. Moreover, the deflection mechanism 46a has at least one second connection member 50a. In the present case, the deflection mechanism 46a has a plurality of second connection members, for example four second connection members. Of the plurality of second connection members, for the sake of clarity only the second connection member 50a is provided with a reference sign. Unless otherwise indicated, the plurality of second connection members are designed substantially identically. A description with respect to the second connection member 50a can thus be applied to the plurality of second connection members. Alternatively, the plurality of second connection members 50a could also be designed differing at least partially from one another.

The second connection member 50a is arranged at least partially coaxially surrounding the first connection member 48a. The second connection member 50a has an external diameter which is greater than an external diameter of the first connection member 48a. The second connection member 50a has a disk-like and/or lens-like shape. The first connection member 48a has an olive-like shape.

The second connection member 50a is symmetrical. The second connection member 50a is designed substantially as a rotation body. The second connection member 50a has a second axis of rotational symmetry 54a. About the second axis of rotational symmetry 54a, the second connection member 50a has at least one two-fold rotational symmetry. For example, a number of a first rotational symmetry could correspond to a number of planes in which the deflectable portion is deflectable. Moreover, a rotational symmetry of the second connection member 50*a* can correspond to that of the first one. In a straight position, the direction of longitudinal extent 38*a* of the shaft 26*a* corresponds to the second axis of rotational symmetry 54*a*. Moreover, in the straight position, the second axis of rotational symmetry 54*a* corresponds to the first axis of rotational symmetry 52*a*.

A difference between a number of the plurality of first connection members and a number of the plurality of second connection members is different than zero. In the present case, the difference corresponds to the value one, such that the plurality of second connection members always comprise one second connection member 50*a* more than the plurality of first connection members comprise first connection members. A number of the plurality of first connection members is odd. A number of the plurality of second connection members is even. In the present case, the plurality of first connection members comprise a total of three first connection members. Moreover, in the present case, the plurality of second connection members comprise a total of four second connection members.

Two of the plurality of second connection members complete the deflectable portion 42*a* of the shaft 26*a*. One of the plurality of second connection members, advantageously a distal one, is connected to the cuff 56*a*. In the present case, the distal second connection member 50*a* is integrally connected to the cuff 56*a*. This second connection member 50*a* connects the deflection mechanism 46*a* at least partially integrally to the end portion 28*a* of the shaft 26*a*.

Another of the plurality of second connection members, advantageously a proximal one, is connected to the further cuff 58*a*. In the present case, the proximal second connection member 50*a* is integrally connected to the further cuff 58*a*. This second connection member 50*a* connects the deflection mechanism 46*a* at least partially integrally to the middle portion 32*a* of the shaft 26*a*.

The first connection member 48*a* and the second connection member 50*a* are configured to interact with each other for a deflection of the shaft 26*a*. The first connection member 48*a* and the second connection member 50*a* are arranged in series.

The plurality of first connection members and the plurality of second connection members are arranged in series. The plurality of first connection members and the plurality of second connection members are arranged in alternation. The plurality of first connection members and the plurality of second connection members are arranged in such a way that a first connection member of the plurality of first connection members is followed by a second connection member of the plurality of second connection members. Moreover, a second connection member of the plurality of second connection members is followed by a first connection member of the plurality of first connection members.

A first connection member of the plurality of first connection members is adjoined by at least one second connection member of the plurality of second connection members. Moreover, a first connection member of the plurality of first connection members is adjoined by two mutually opposite second connection members of the plurality of second connection members. Each of the plurality of first connection members is adjoined by two second connection members of the plurality of second connection members.

A second connection member of the plurality of second connection members is adjoined by at least one first connection member of the plurality of first connection members. Moreover, a second connection member of the plurality of second connection members is adjoined by two mutually opposite first connection members of the plurality of second connection members. Except for the second connection members completing the deflection mechanism, each of the plurality of second connection members is adjoined by two first connection members of the plurality of first connection members.

FIG. 4 shows a schematic sectional view of a part of the endoscopic device 16*a* located in a straight position. Moreover, FIG. 3 shows a schematic sectional view of a part of the endoscopic device 16*a* located in a deflection position.

The first connection member 48*a* and the second connection member 50*a* interact in the manner of a ball joint and/or of vertebral bodies. The first connection member 48*a* has at least one joint head 60*a*. The second connection member 50*a* has at least one joint socket 62*a*. The joint socket 62*a* is designed corresponding to the joint head 60*a*. In this way, the joint head 60*a* of the first connection member 48*a* and the joint socket 62*a* of the second connection member 50*a* engage in each other, such that the first connection member 48*a* and the second connection member 50*a* are mounted movably relative to each other. A reverse embodiment is also conceivable in which a first connection member has a joint socket and the second connection member has a joint head 60*a*.

In the present case, the first connection member 48*a* has two opposite joint heads 60*a*. Of said joint heads, for the sake of clarity only the joint head 60*a* is provided with a reference sign. The joint heads are designed substantially identical to each other. In the present case, the second connection member 50*a* has two opposite joint sockets 62*a*. Of said joint sockets, for the sake of clarity only the joint socket 62*a* is provided with a reference sign. The joint sockets 62*a* are designed substantially identical to each other. Only the second connection members of the plurality of second connection members that complete the deflection mechanism 46*a* have only a single joint socket 62*a* each.

A first connection member 48*a* of the plurality of first connection members is at all times engaged from two opposite sides by two second connection members of the plurality of second connection members. To put it another way, opposite joint heads of an individual first connection member 48*a* of the plurality of first connection members are in each case engaged by a joint socket 62*a* of two second connection members of the plurality of second connection members. In this way, two joint sockets of two separate second connection members of the plurality of second connection members bear on two joint heads of an individual first connection member 48*a* of the plurality of first connection members.

Moreover, two first connection members at all times engage from two opposite sides in a second connection member 50*a* of the plurality of second connection members. To put it another way, joint heads of two first connection members of the plurality of first connection members each engage in one of the opposite joint sockets 62*a* of a second connection member 50*a* of the plurality of second connection members. In this way, two joint heads of two separate first connection members of the plurality of first connection members bear on two joint sockets of an individual second connection member 50*a* of the plurality of second connection members.

Only the second connection members of the plurality of second connection members that complete the deflection mechanism 46*a* engage around only a single first connection member 48*a* of the plurality of first connection members. To put it another way, only one joint head 60*a* of a single first connection member 48*a* of the plurality of first connection members engages in each case in the single joint socket 62*a* of the second connection member 50a of the plurality of second connection members that completes the deflection mechanism. In this way, only a single joint head of a first connection member 48a of the plurality of first connection members bears in a single joint head 60a of an individual second connection member 50a of the plurality of second connection members that completes this deflection mechanism 46a.

In the straight position, which is shown for example in FIGS. 2 and 4, a first axis of rotational symmetry 52a of the first connection member 48a and a second axis of rotational symmetry 54a of the second connection member 50a correspond to each other. In the deflection position, which is shown for example in FIGS. 3 and 5, the direction of principal extent of the first connection member 48a and that of the second connection member 50a are arranged at an angle to each other. In the deflection position, an angle between the first axis of rotational symmetry 52a of the first connection member 48a and the second axis of rotational symmetry 54a of the second connection member 50a is at most 15°. A maximum angle is limited here by the fact that two of the plurality of second connection members engaging around a first connection member of the plurality of first connection members about each other.

The first connection member 48a has a first geometric midpoint 64a. Moreover, the second connection member 50a has a second geometric midpoint 66a. In the straight position, the first geometric midpoint 64a and the second geometric midpoint 66a are arranged offset relative to each other along the direction of longitudinal extent 38a of the shaft 26a. In the straight position, a straight-position spacing 68a exists between the first connection member and second connection member. The straight-position spacing 68a is defined by a shortest connection between the first geometric midpoint 64a of the first connection member 48a and the second geometric midpoint 66a of the second connection member 50a.

In the deflection position, the first geometric midpoint 64a and the second geometric midpoint 66a are arranged offset relative to each other. In the deflection position, a deflection spacing 70a exists between the first connection member 48a and second connection member 50a. In the deflection position, the deflection spacing 70a is defined by a shortest connection between the first geometric midpoint 64a of the first connection member 48a and the second geometric midpoint 66a of the second connection member 50a. In the present exemplary embodiment, the deflection-position spacing 70a in the deflection position is equal to the straight-position spacing 68a in the straight position. Alternatively, however, the deflection spacing could also be greater or less than the straight-position spacing 68a, for example depending on an embodiment of the connection members.

The first connection member 48a has at least one outer contour 72a. The outer contour 72a partially forms the joint head 60a of the first connection member 48a. The outer contour 72a is directed outward. The outer contour 72a faces in the direction of an environment of the shaft 26a. The design of the outer contour 72a differs from concave. In the present case, the outer contour 72a is of convex design. The outer contour 72a corresponds to an arc of a circle 76a. Alternatively, the outer contour could have at least in part a shape different from the shape of an arc of a circle, being designed for example in the form of a circle involute, a cycloid, a paraboloid and/or an ellipsoid.

There exists a diameter 74a of a smallest arc of a circle 76a still just completely enclosing the outer contour 72a of the first connection member 48a. In the present exemplary embodiment, this diameter 74a corresponds substantially to a maximum width of the first connection member. Here, the width is measured perpendicular to the first axis of rotational symmetry 52a and/or to the direction of longitudinal extent 38a of the shaft 26a. However, it is also conceivable that a diameter is different from a width and is for example greater than the latter.

The second connection member 50a has at least one inner contour 78a. The inner contour 78a at least partially forms the joint socket 62a of the second connection member 50a. The inner contour 78a of the second connection member 50a is configured for interaction with the outer contour 72a of the first connection member. The outer contour 72a of the first connection member 48a and the inner contour 78a of the second connection member 50a lie opposite each other. The outer contour 72a and the inner contour 78a bear at most partially on each other. The inner contour 78a of the second connection member 50a is designed corresponding to the outer contour 72a of the first connection member 48a. The inner contour 78a is directed inward. The design of the inner contour 78a differs from concave. Moreover, in the present case, the inner contour 78a is straight. Alternatively, an inner contour could be designed corresponding at least partially to an in particular convex shape of a circle involute, an arc of a circle, a cycloid, a paraboloid and/or an ellipsoid.

The deflection mechanism 46a has at least one control train 80a. In the present case, the deflection mechanism 46a has a plurality of control trains 80a, for example at least three control trains. Of said plurality of control trains, for the sake of clarity only the control train 80a is provided with a reference sign. The plurality of control trains are arranged offset relative to one another along a circumference of the shaft 26a. The plurality of control trains extend substantially parallel to one another. Moreover, the plurality of control trains are arranged coaxially surrounding at least the first connection member or even the plurality of first connection members. The plurality of control trains are here designed substantially identically, such that a description with respect to the control train 80a can be applied to the plurality of control trains. Alternatively, the plurality of control trains could also be designed at least partially different from one another.

The control train 80a is configured for an adjustment of a deflection of the deflectable portion 42a of the shaft 26a. The control train 80a can be actuated by means of an actuator system. For the sake of clarity, the actuator system is not shown here. The actuator system can be part of the endoscopic device 16a or also part of the surgical robot 12a, for example of the robot arm 18a. The control train 80a extends at least partially through the shaft 26a. In the present case, the control train 80a extends through the entire shaft 26a. Moreover, the control train 80a even extends partially beyond the shaft 26a, for example in order to be coupled to an actuator system.

The control train 80a is coupled to the connection members 48a, 50a. The connection members 48a, 50a are arranged in a row on the control train 80a. At least in the straight position, the control train 80a keeps the connection members 48a, 50a pretensioned. Alternatively or in addition, a control train could be configured for a rotation of a shaft.

The control train 80a is designed to be flexurally slack. In the present case, the control train 80a is designed as a wire. The control train 80a is formed from a cord, for example a metal cord. The control train 80a has a diameter 74a. The diameter can be at least 2.5% and/or at most 25% of an external diameter of the shaft 26a. In the present case, the diameter 74a measures 0.36 mm, for example.

The control train 80a is guided substantially parallel to the shaft 26a. The control train 80a extends at least partially parallel to a direction of longitudinal extent 38a of the shaft 26a. Moreover, the control train 80a is guided in doubled form. The control train 80a is divided into a portion which is guided in the direction of the end portion 28a and away from the further end portion 30a, and a portion which is guided away from the end portion 28a and in the direction of the further end portion 30a.

For guiding the control train 80a, the second connection member 50a has at least one passageway 82a. The passageway 82a has at least funnel-shaped or two funnel-shaped openings. In the present case, the second connection member has a plurality of passageways of which, for the sake of clarity, only the passageway 82a is provided with a reference sign. The plurality of passageways are arranged offset relative to each other along a circumference of the second connection member 50a. The plurality of passageways are substantially identical to one another, such that a description with respect to the passageway 82a can be applied to the plurality of passageways. Alternatively, the plurality of passageways could also be designed at least partially different from one another.

In each case, two passageways of the second connection member 50a guide one control train 80a. A passageway 82a of the second connection member 50a guides a portion of the control train 80a guided away from the further end portion 30a, and a further passageway 82a of the second connection member 50a guides a portion of the control train 80a guided away from the end portion 28a.

FIG. 6 shows a schematic perspective view of a part of the endoscopic device 16a in a partially dismantled state. The control train 80a is connected to the end portion 28a of the shaft 26a. In the region of the end portion 28a of the shaft 26a, a part of the control train 80a is arranged to form a loop-back 84a.

The end portion 28a of the shaft 26a has at least one train receptacle 86a. The train receptacle 86a is arranged on the cuff 56a. The control train 80a is arranged at least partially in the train receptacle 86a. The part of the control train 80a forming the loop-back 84a is arranged in the train receptacle 86a. Before the loop-back 84a, the train receptacle 86a guides the control train 80a in the direction of the end portion 28a of the shaft 26a. After the loop-back 84a, the train receptacle 86a guides the control train 80a back again from the end portion 28a of the shaft 26a. The train receptacle 86a has at least one passageway 88a for at least an axial engagement of the control train 80a.

In the present case, the train receptacle 86a has a plurality of passageways. For the sake of clarity, of the passageways only the passageway 88a is provided with a reference sign. The passageways are arranged on the cuff 56a. The passageways are arranged offset relative to one another in the circumferential direction of the shaft 26a. In each case, two passageways of the end portion 28a guide a control train 80a. Alternatively, instead of a looped-back control train, two individual control trains could be used. A passageway 82a of the second connection member 50a guides a portion of the control train 80a guided away from the further end portion 30a, and a further passageway 88a of the second connection member 50a guides a portion of the control train 80a guided away from the end portion 28a.

The endoscopic device 16a has at least one end effector 90a. in FIGS. 2 and 4, the end effector 90a is shown in a closed operating state. In FIGS. 3 and 5, the end effector 90a is shown in an opened operating state. In the present case, the endoscopic device 16a has precisely one end effector 90a. The end effector 90a is arranged on an end portion 28a of the shaft 26a. The end effector 90a is connected at least partially integrally to the end portion 28a of the shaft 26a. In the present case, the end effector 90a is designed in the form of forceps. The end effector 90a can also be designed in the form of scissors, a clamp, forceps, a scalpel, a coagulator, a stapler, a test hook or the like. An end effector could be configured to be electrically conductive, in order advantageously to transmit current. For example, an end effector could thus be unipolar, bipolar or the like.

The end effector 90a comprises at least one tool piece 92a. In the present case, the end effector 90a has at least one further tool piece 94a. The further tool piece 94a is configured for interaction with the tool piece 92a. The further tool piece 94a is substantially identical to the tool piece 92a. In the present case, the end effector 90a comprises two tool pieces 92a, 94a in total. A tool piece could be a scissor blade, a cutting edge, an electrode or another tool piece, in particular a surgical tool piece. In the present case, the tool piece 92a, 94a forms a jaw part. The jaw part is a branch. The branch can be adapted to a specific purpose of use.

The end effector 90a has an end-effector head 96a. The end-effector head 96a is connected integrally to an end portion 28a of the shaft 26a. The end-effector head 96a is formed integrally with the cuff 56a. Moreover, the end-effector head 96a is integrally connected to the second connection member that distally completes the deflection mechanism 46a.

The end-effector head 96a has an end-effector fork 98a. The end-effector fork 98a comprises at least one end-effector limb 100a. Moreover, the end-effector fork 98a comprises a further end-effector limb 102a. The end-effector limb 100a and the further end-effector limb 102a are arranged lying opposite each other. The end-effector limb 100a and the further end-effector limb 102a are connected to each other. The end-effector limb 100a and the further end-effector limb 102a of the end-effector head 96a are integrally connected to each other.

The end-effector head 96a defines an end-effector bushing 104a of the end effector 90a. Further components of the endoscopic device 16a, for example a movement transducer 116a, can be arranged in the end-effector bushing 104a.

The endoscopic device 16a has at least one actuation train 106a. In the present case, the endoscopic device 16a has precisely one actuation train 106a. The actuation train 106a is configured for actuation of the end effector 90a. The actuation train 106a can be actuated by means of an actuator system. The actuator system can be part of the endoscopic device 16a or also part of the surgical robot 12a, specifically of the robot arm 18a for example.

The actuation train 106a extends at least partially through the shaft 26a. The actuation train 106a extends centrally through the shaft 26a. In the present case, the actuation train 106a extends through the entre shaft 26a. Moreover, the actuation train 106a even extends partially beyond the shaft 26a, for example in order to be coupled to an actuator system.

The actuation train 106a is at least partially flexible. The actuation train 106a has at least one flexible portion 108a. The actuation train 106a is at least partially inflexible. Moreover, the actuation train 106a has at least one inflexible portion 110a. The inflexible portion 110a is less flexible compared to the flexible portion 108a. The flexible portion 108a is arranged following the inflexible portion 110a.

The actuation train 106a is arranged in the shaft 26a in such a way that the flexible portion 108a of the actuation train 106a is congruent with the deflectable portion 42a of the shaft 26a. The actuation train 106a is therefore flexible in the region of the deflectable portion 42a of the shaft 26a.

The actuation train 106a has at least one inner cable 112a. The inner cable 112a is designed as a cord. Alternatively, the inner cable could also have a solid wire. The inner cable 112a is configured at least for a mechanical force transmission. The inner cable 112a is at least partially flexible, for example in the flexible portion of the actuation train 106a. In the present case, the inner cable 112a is flexible over the full extent of the actuation train 106a.

The actuation train 106a has at least one reinforcement 114a. The reinforcement 114a stiffens the actuation train 106a at least partially. The reinforcement 114a stiffens the actuation train 106a at least in a region of the shaft 26a different from the flexible portion 108a. The reinforcement 114a partially stiffens the inner cable 112a. The reinforcement 114a is arranged coaxially surrounding the inner cable 112a. The reinforcement 114a is designed as a tube. The reinforcement 114a is formed at least partially from a metal. Alternatively or in addition, the reinforcement 114a can be formed at least partially from a plastic. The reinforcement 114a is arranged in the inflexible portion 110a of the actuation train 106a. By contrast, the flexible portion 108a of the actuation train 106a is free of a reinforcement 114a.

The endoscopic device 16a has at least one movement transducer 116a. In the present case, the endoscopic device 16a has precisely one movement transducer 116a. The movement transducer 116a is configured to couple the end effector 90a and the actuation train 106a at least mechanically to each other. Alternatively, it would be conceivable that the movement transducer also connects the end effector and the actuation train electrically to each other.

The movement transducer 116a is configured to convert a movement of the actuation train 106a into a movement of at least one tool piece 92a. The movement of the actuation train 106a is a linear movement. The movement of the tool piece 92a is a pivoting movement. It would be conceivable that the further tool piece 94a is arranged fixedly or, in other words, is immovable. In the present case, however, the further tool piece 94a is also coupled to the actuation train 106a via the movement transducer 116a. The movement transducer 116a is configured to convert a movement of the actuation train 106a into a movement of the further tool piece 94a. The movement of the further tool piece 94a is a pivoting movement.

Independently of an operating state, the movement transducer 116a is arranged such that it cannot emerge from inside at least one part of the end effector 90a. In the present case, the movement transducer 116a is arranged at least largely in the end-effector head 96a, independently of an operating state. The movement transducer 106a is arranged at least largely in the end-effector bushing 104a of the end-effector head 96a, independently of an operating state. Independently of an operating state, the end-effector head 96a, in a side view, at least largely covers the movement transducer 116a. The movement transducer 116a is covered laterally by the end-effector fork 98a, since it is arranged congruent with the end-effector limbs 100a, 102a of the end-effector fork 98a. In the present case, in a side view, at least one end-effector limb 100a, 102a of the end-effector fork 98a of the end-effector head 96a at least largely covers the movement transducer.

The movement transducer 116a defines at least one pivot axis 118a. The pivot axis 118a is configured for the pivoting of the tool piece 92a. The pivot axis 118a is oriented at least substantially perpendicular to an axis of principal extent 120a of the end effector 90a. The pivot axis 118a is arranged offset laterally with respect to an axis of principal extent 120a of the end effector 90a. To put it another way, the axis of principal extent 120a of the end effector 90a and the pivot axis 118a do not intersect. Moreover, an imaginary plane exists which is parallel to the axis of principal extent 120a of the end effector 90a and on which the pivot axis 118a is oriented substantially perpendicularly.

The movement transducer 116a has a mechanical force path. By way of the mechanical force path, the movement transducer 116a transmits a force from the actuation train 106a at least to the tool piece 92a of the end effector 90a. In the present case, the movement transducer 106a has at least one further mechanical force path. By way of the further mechanical force path, the movement transducer transmits a force from the actuation train 106a to the further tool piece 94a of the end effector 90a.

The movement transducer 116a comprises at least one push and/or pull piston 122a. In the present case, the movement transducer 116a comprises precisely one push and/or pull piston 122a. Independently of an operating state, the push and/or pull piston 122a is arranged at least largely in the end-effector bushing 104a. In a side view, the push and/or pull piston 122a is concealed by the end-effector fork 98a, for example by the end-effector limb 100a and/or the further end-effector limb 102a of the end-effector fork 98a. The push and/or pull piston 122a is at least connected to the actuation train 106a for the force transmission. Moreover, the push and/or pull piston 122a could be connected electrically to the actuation train 106a.

The push and/or pull piston 122a is guided linearly. The end-effector head 96a has a piston guide 126a. The piston guide 126a is designed corresponding to at least one part of the push and/or pull piston 122a. The piston guide 126a is configured for a linear guiding of the push and/or pull piston 122a. The push and/or pull piston 122a has a bolt 124a. The bolt 124a has a cylindrical shape. The bolt 124a is arranged in a piston guide 126a of the end-effector head 96a.

The actuation train 106a and the push and/or pull piston 122a are connected to each other at least by form-fit and/or force-fit engagement. In the present case, the actuation train 106a and the push and/or pull piston 122a are even connected to each other by frictional engagement. The actuation train 106a and the push and/or pull piston 122a are connected to each other by a plastic deformation of the push and/or pull piston 122a and/or of the actuation train 106a. The push and/or pull piston 122a and/or the actuation train 106a are crimped to each other. In the present case, the bolt 124a of the push and/or pull piston 122a is designed for connection to the actuation train 106a.

The bolt 124a of the push and/or pull piston 122a defines an actuation train receptacle 128a. The actuation train 106a is inserted partially into the actuation train receptacle 128a. The bolt 124a is pressed together with the actuation train 106a. In this way, the actuation train 106a is pressed into the bolt 124a. Alternatively or in addition, the actuation train and the push and/or pull piston could be connected to each other at least by cohesive bonding. For example, the actuation train and the push and/or pull piston could be soldered and/or adhesively bonded to each other. For example, the bolt 124a has filling holes into which an adhesive or soldering tin can be inserted for cohesively bonded connection into the actuation train receptacle.

The push and/or pull piston 122a has an armature 130a. The armature 130a is substantially plate-shaped. The armature 130a has the shape of a substantially circular contour. The end-effector fork 98a forms an abutment for the armature 130a. The armature 130a is greater in at least one dimension than the piston-guide receptacle. In this way, the armature 130a limits a linear movement of the push and/or pull piston 122a or of the actuation train 106a. The armature 130a is arranged in the end-effector bushing 104a. In a side view, the armature 130a is concealed by the end-effector fork 98a, for example by the end-effector limb 100a and/or the further end-effector limb 102a of the end-effector fork 98a. The armature 130a is connected to the bolt 124a.

The push and/or pull piston 122a is formed at least partially integrally. In the present case, the armature 130a and the bolt 124a of the push and/or pull piston 122a are integrally connected to each other. Alternatively, the push and/or pull piston could also be designed in multiple parts. In the present case, the armature 130a and the bolt 124a are connected integrally to each other. The push and/or pull piston 122a is formed at least partially from metal. For example, the push and/or pull piston 122a can also be an injection-molded component.

The movement transducer 116a has at least one pivot lever 132a. The pivot lever 132a is connected at least mechanically to the push and/or pull piston 122a. The pivot lever 132a is connected to the end effector 90a. The pivot lever 132a is connected to the tool piece 92a. In the present case, the pivot lever 132a is connected integrally to the tool piece 92a. The pivot lever 132a is arranged at least partially in the end-effector bushing 104a. In the present case, the pivot lever 132a is arranged at least partially in the end-effector bushing 104a. In a side view, the pivot lever 132a is concealed by the end-effector fork 98a, for example by the end-effector limb 100a and/or the further end-effector limb 102a of the end-effector fork 98a. The pivot lever 132a bears on the push and/or pull piston 122a, specifically for example on the armature 130a of the push and/or pull piston 122a.

The pivot lever 132a has a pivot lever main body 134a. The pivot lever main body 134a is substantially plate-shaped. In a side view, the pivot lever main body 134a has a circular contour. The pivot lever main body 134a is formed integrally with the tool piece 92a.

The movement transducer 116a has a coupling mechanism 136a. The coupling mechanism 136a is configured at least for a mechanical coupling of the pivot lever 132a and of the push and/or pull piston 122a. The coupling mechanism 136a is formed at least partially by the pivot lever 132a. Moreover, the coupling mechanism 136a is formed at least partially by the push and/or pull piston 122a. The coupling mechanism 136a has at least one coupling element 138a. The coupling mechanism 136a has at least one corresponding coupling element 140a. The corresponding coupling element 140a is designed corresponding to the coupling element 138a. The coupling element 138a and the corresponding coupling element 140a together define the pivot axis 118a of the movement transducer 116a, which is oriented at least substantially perpendicular to an axis of principal extent 120a of the end effector 90a and is arranged laterally offset relative to the latter.

The coupling element 138a is part of the push and/or pull piston 122a. The coupling element 138a is arranged on the armature 130a of the push and/or pull piston 122a. The coupling element 138a is connected rigidly to the armature 130a. The coupling element 138a is arranged offset relative to a geometric midpoint 64a, 66a of the armature 130a. The coupling element 138a is arranged offset relative to the axis of principal extent 120a. In the present case, the coupling element 138a is designed as a cam.

The corresponding coupling element 140a is part of the pivot lever 132a. The corresponding coupling element 140a is arranged on the pivot lever main body 134a and/or connected thereto. The corresponding coupling element 140a is arranged offset relative to a geometric midpoint 64a, 66a of the pivot lever main body 134a. The corresponding coupling element 140a is arranged offset relative to the axis of principal extent 120a of the end effector 120a. In the present case, the corresponding coupling element 140a is designed as a cam carrier, for example in the form of a laterally opened recess of the pivot lever 132a. When the push and/or pull piston 122a and the pivot lever 132a are coupled to each other by means of the coupling mechanism 136a, the coupling element 138a and the corresponding coupling element 140a engage in each other and make mutual contact. Alternatively, the embodiments of the coupling element and of the corresponding coupling element could also be changed around. For example, the coupling element could thus be designed as a cam carrier and the corresponding coupling element could be designed as a cam.

The movement transducer 116a has a rotary bearing 142a. The rotary bearing 142a is configured at least for a rotary mounting of the tool piece 92a relative to the end-effector head 96a. The rotary bearing 142a is formed at least partially by the pivot lever 132a. Moreover, the rotary bearing 142a is formed at least partially by the end-effector head 96a. The rotary bearing 142a has at least one bearing element 144a. The rotary bearing 142a has at least one corresponding bearing element 146a. The corresponding bearing element 146a is designed corresponding to the bearing element 144a. The bearing element 144a and the corresponding bearing element 146a together define a rotary axis 148a about which the tool piece 92a rotates upon actuation of the tool piece 92a. The rotary axis 148a is oriented at least substantially perpendicular to an axis of principal extent 120a of the end effector 90a and is arranged laterally offset relative thereto. Moreover, the rotary axis 148a is arranged substantially parallel to the pivot axis 118a. In relation to an axis of principal extent 120a of the end effector 90a, the rotary axis 148a lies opposite the pivot axis 118a.

The bearing element 144a is part of the pivot lever 132a. The bearing element 144a is arranged on the pivot lever main body 134a and/or connected thereto. The bearing element 144a is arranged offset relative to a geometric midpoint 64a, 66a of the pivot lever main body 134a. The bearing element 144a is arranged offset relative to the axis of principal extent 120a of the end effector 90a. The bearing element 144a lies opposite the corresponding coupling element 140a. In the present case, the bearing element 144a is designed as a cam.

The corresponding bearing element 146a is part of the end-effector head 96a. The corresponding bearing element 146a is arranged on the end-effector limb 100a of the end-effector fork 98a and/or connected thereto. The corresponding bearing element 146a is arranged offset relative to a geometric midpoint 64a, 66a of the end-effector limb 100a. The corresponding bearing element 146a is arranged offset relative to the axis of principal extent 120a of the end effector 90a. In the present case, the corresponding bearing element 146a is designed as a cam carrier, for example in the form of a laterally opened recess of the end-effector limb 100a. When the pivot lever 132a and the end-effector head 96a are mounted rotatably to each other by means of the rotary bearing 142a, the bearing element 144a and the corresponding coupling element 140a engage in each other and make mutual contact. Alternatively, the embodiments of the bearing element and of the corresponding bearing element could also be changed around. For example, the bearing element could thus be designed as a cam carrier and the corresponding bearing element could be designed as a cam.

The movement transducer 116a has at least one further pivot lever 150a. The further pivot lever 150a is connected at least mechanically to the push and/or pull piston 122a. The further pivot lever 150a is connected to the end effector 90a. The further pivot lever 150a is connected to the further tool piece 94a. In the present case, the further pivot lever 150a is connected integrally to the further tool piece 94a. The further pivot lever 150a is arranged at least partially in the end-effector bushing 104a. In the present case, the further pivot lever 150a is arranged at least partially in the end-effector bushing 104a. In a side view, the further pivot lever 150a is concealed by the end-effector fork 98a, for example by the end-effector limb 100a and/or the further end-effector limb 102a of the end-effector fork 98a. The further pivot lever 150a bears on the push and/or pull piston 122a, specifically for example on the armature 130a of the push and/or pull piston 122a. The further pivot lever 150a bears on the push and/or pull piston 122a on a side lying opposite the pivot lever 132a.

The further pivot lever 150a has a further pivot lever main body 152a. The further pivot lever main body 152a is plate-shaped. In a side view, the further pivot lever main body 152a has a circular contour. The further pivot lever main body 152a is formed integrally with the further tool piece 94a.

The movement transducer 116a has a further coupling mechanism 154a. The further coupling mechanism 154a is configured at least for a mechanical coupling of the further pivot lever 150a and of the push and/or pull piston 122a. The further coupling mechanism 154a is formed at least partially by the further pivot lever 150a. Moreover, the further coupling mechanism 154a is formed at least partially by the push and/or pull piston 122a. The further coupling mechanism 154a has at least one further coupling element 156a. The further coupling mechanism 154a has at least one further corresponding coupling element 158a. The further corresponding coupling element 158a is designed corresponding to the coupling element 156a. The further coupling element 156a and the further corresponding coupling element 158a together define the further pivot axis 160a of the movement transducer 116a, which is oriented at least substantially perpendicular to an axis of principal extent 120a of the end effector 90a and is laterally offset relative thereto. In relation to the axis of principal extent 120a, the further pivot axis 160a lies opposite the pivot axis 118a. The further pivot axis 160a is substantially parallel to the pivot axis 108a.

The further coupling element 156a is part of the push and/or pull piston 122a. The further coupling element 156a is arranged on the armature 130a of the push and/or pull piston 122a. The further coupling element 156a is arranged on the side of the armature 130a lying opposite the side on which the coupling element 138a is arranged. The further coupling element 156a is connected rigidly to the armature 130a. The further coupling element 156a is arranged offset relative to a geometric midpoint 64a, 66a of the armature 130a. The further coupling element 156a is arranged offset relative to the axis of principal extent 120a. In the present case, the further coupling element 156a is designed as a cam.

The further corresponding coupling element 158a is part of the further pivot lever 150a. The further corresponding coupling element 158a is arranged on the further pivot lever main body 152a and/or connected thereto. The further corresponding coupling element 158a is arranged offset relative to a geometric midpoint 64a, 66a of the further pivot lever main body 152a. The further corresponding coupling element 158a is arranged offset relative to the axis of principal extent 120a of the end effector 90a. In the present case, the further corresponding coupling element 158a is designed as a cam carrier, for example in the form of a laterally opened recess of the further pivot lever 150a. When the push and/or pull piston 122a and the further pivot lever 150a are coupled to each other by means of the further coupling mechanism 154a, the further coupling element 156a and the corresponding coupling element 158a engage in each other and make mutual contact. Alternatively, the embodiments of the further coupling element and of the further corresponding coupling element could also be changed around. For example, the further coupling element could thus be designed as a cam carrier and the further corresponding coupling element could be designed as a cam.

The movement transducer 116a has a further rotary bearing 162a. The further rotary bearing 162a is configured at least for a rotary mounting of the further tool piece 94a relative to the end-effector head 96a. The further rotary bearing 162a is formed at least partially by the further pivot lever 150a. Moreover, the further rotary bearing 162a is formed at least partially by the end-effector head 96a. The further rotary bearing 162a has at least one further bearing element 164a. The further rotary bearing 162a has at least one further corresponding bearing element 166a. The further corresponding bearing element 166a is designed corresponding to the further bearing element 164a. The further bearing element 164a and the further corresponding bearing element 166a together define a further rotary axis 168a about which the further tool piece 94a rotates upon actuation of the further tool piece 94a. The further rotary axis 168a is oriented at least substantially perpendicular to an axis of principal extent 120a of the end effector 90a and is arranged laterally offset relative thereto. Moreover, the further rotary axis 168a is arranged substantially parallel to the further pivot axis 160a. In relation to an axis of principal extent 120a of the end effector 90a, the further rotary axis 168a lies opposite the further pivot axis 160a.

The further bearing element 164a is part of the further pivot lever 150a. The further bearing element 164a is arranged on the further pivot lever main body 152a and/or connected thereto. The further bearing element 164a is arranged offset relative to a geometric midpoint 64a, 66a of the further pivot lever main body 152a. The further bearing element 164a is arranged offset relative to the axis of principal extent 120a of the end effector 90a. The further bearing element 164a lies opposite the corresponding further coupling element 156a. In the present case, the further bearing element 164a is designed as a cam.

The further corresponding bearing element 166a is part of the end-effector head 96a. The further corresponding bearing element 166a is arranged on the further end-effector limb 102a of the end-effector fork 98a and/or connected thereto. The further corresponding bearing element 166a is arranged offset relative to a geometric midpoint 64a, 66a of the further end-effector limb 102a. The further corresponding bearing element 166a is arranged offset relative to the axis of principal extent 120a of the end effector 90a. In the present case, the further corresponding bearing element 166a is designed as a cam carrier, for example in the form of a laterally opened recess of the further end-effector limb 102a. When the further pivot lever 150a and the end-effector head 96a are mounted rotatably to each other by means of the further rotary bearing 162a, the further bearing element 164a and the further corresponding coupling element 158a engage in each other and make mutual contact. Alternatively, the embodiments of the further bearing element and of the further corresponding bearing element could also be changed around. For example, the further bearing element could thus be designed as a cam carrier and the further corresponding bearing element could be designed as a cam.

The movement transducer 116a has a guide bearing 170a. The guide bearing 170a is configured to guide constituent parts of the movement transducer 116a. For guiding of the pivot lever 132a, the guide bearing 170a has a slotted guide 172a. The slotted guide 172a is designed in the form of a curved oblong hole. The slotted guide 172a is defined by the pivot lever 132a. The slotted guide 172a extends through a geometric midpoint 64a, 66a of the pivot lever 132a. The slotted guide 172a is formed by a recess of the pivot lever main body 134a.

For guiding the further pivot lever 150a, the guide bearing 170a has a further slotted guide 174a. The further slotted guide 174a is designed in the form of a curved oblong hole. Compared to the slotted guide 172a, the further slotted guide 174a is at least rotated through 180°. The further slotted guide 174a is defined by the further pivot lever 150a. The further slotted guide 174a extends through a geometric midpoint 64a, 66a of the further pivot lever 150a. The further slotted guide 174a is formed by a recess of the further pivot lever main body 152a.

For guiding the push and/or pull piston 122a, the guide bearing 170a has an additional slotted guide 176a. The additional slotted guide 176a is designed in the form of a straight oblong hole. The additional slotted guide 176a is defined by the push and/or pull piston 122a. The further slotted guide 174a extends through a geometric midpoint 64a, 66a of the armature 130a of the push and/or pull piston 122a. The additional slotted guide 176a is formed by a recess of the further armature 130a.

The guide bearing 170a moreover comprises a guide pin 178a. The guide pin 178a is arranged extending through the slotted guide 172a. Moreover, the guide pin 178a is arranged extending through the additional slotted guide 176a. Moreover, the guide pin 178a is arranged extending through the further slotted guide 174a. The guide pin 178a is connected to the end-effector head 96a, specifically for example to the end-effector fork 98a. The end-effector limb 100a of the end-effector fork 98a has a pin receptacle 180a. The pin receptacle is designed for form-fit and/or force-fit connection to the guide pin 178a. Moreover, the further end-effector limb 102a of the end-effector fork 98a has a further pin receptacle 182a. The further pin receptacle 182a is designed for from-fit and/or force-fit connection to the guide pin 178a. In a mounted state, the guide pin 178a extends through the pin receptacle 180a, the slotted guide 172a, the additional slotted guide 176a, the further slotted guide 174a and the further pin receptacles 182a. The guide pin 178a secures the pivot lever, the further pivot lever 150a and the push and/or pull piston 122a on the end-effector head 96a.

FIGS. 7 to 27 show further exemplary embodiments according to the disclosure. The following descriptions and the drawings are substantially restricted to the differences between the exemplary embodiments, wherein, in respect of components with the same label, in particular in respect of components with the same reference signs, reference is also made, as a matter of principle, to the drawings and/or the description of the other exemplary embodiments, in particular of FIGS. 1 to 6. All combinations of the exemplary embodiments mentioned here should also be considered disclosed. In order to distinguish the exemplary embodiments, the letter a has been appended to the reference signs of the exemplary embodiment in FIGS. 1 to 6. In the exemplary embodiments of FIGS. 7 to 27, the letter a has been replaced by the letters b to j.

FIG. 7 shows schematically a further exemplary embodiment of at least one part of an endoscopic device 16b according to the principles of the present disclosure, in a sectional view along a shaft 26b of the endoscopic device 16b. The present exemplary embodiment differs from the preceding one essentially in terms of an electrification of the endoscopic device 16b.

The endoscopic device 16b has an actuation train 106b. The actuation train 106b has at least one electrical pole conductor 184b. The electrical pole conductor 184b is configured to provide at least one electrical potential for at least one tool piece 92b of an end effector 90b of the endoscopic device 16b. The electrical pole conductor 184b is designed as an inner conductor. The electrical pole conductor 184b is formed by an inner cable 112b of the actuation train 106b. It is conceivable that the electrical pole conductor can be configured to provide an equal electrical potential for the tool piece and the further tool piece.

The actuation train 106b has at least one further electrical pole conductor 186b. The further electrical pole conductor 186b is configured to provide at least one further electrical potential for a further tool piece 94b of the end effector 90b of the endoscopic device 16b. The electrical pole conductor 184b has a principal extent. Moreover, the further electrical pole conductor 186b has a further principal extent. The principal extent of the electrical pole conductor 184b is greater than a further principal extent of the further electrical pole conductor 186b. The further electrical pole conductor 186b is designed separately from the electrical pole conductor 184b. The further electrical pole conductor 186b is configured to provide at least one further electrical potential. The further electrical pole conductor 186b coaxially surrounds the electrical pole conductor 184b. The further electrical pole conductor 186b is designed as an outer conductor. The further electrical pole conductor 186b has a tubular design. The further electrical pole conductor 186b is formed at least partially from a braid. The actuation train 106b has an outer cable 188b. The outer cable 188b is arranged surrounding the inner cable 112b. The outer cable 188b forms the further electrical pole conductor 186b.

FIG. 8 shows schematically at least one part of the endoscopic device 16b in a sectional view transverse to the shaft 26b. The actuation train 106b has at least one electrical insulator 190b. The electrical insulator 190b is formed at least partially from an insulation material. The insulation material has a CTI value of at least 150. In the present case, the insulation material even has a CTI value of more than 600. The insulation material can be PEEK, for example. In the present case, the insulation material is a tetrafluoroethylene-hexafluoropropylene copolymer (FEP) or a perfluoralkoxy polymer (PFA). The plastic can be flexible and/or elastic. The electrical insulator 190b coaxially surrounds the electrical pole conductor 184b. The electrical insulator 190b is arranged between the electrical pole conductor 184b and the further electrical pole conductor 186b. The actuation train 106b has at least one further electrical insulator 192b. The further electrical insulator 192b coaxially surrounds the further electrical pole conductor 186b.

The endoscopic device 16b has a movement transducer 116b (cf. FIG. 7). The movement transducer 116b is configured to mechanically couple the end effector 90b and the actuation train 106b. In the present exemplary embodiment, the movement transducer 116b is additionally configured to electrically couple the end effector 90b and the actuation train 106b. The movement transducer 116b connects at least the electrical pole conductor 184b to the tool piece 92b. In the present case, the movement transducer 116b connects the electrical pole conductor 184b electrically to the tool piece 92b. Moreover, the movement transducer 116b connects the further electrical pole conductor 186b electrically to the further tool piece 94b.

A mechanical force path of the movement transducer 116b, by way of which a force is transmitted from the actuation train 106b to the tool piece 92b, and an electrical conduction path of the movement transducer 116b, by way of which the electrical potential is transmitted to the tool piece 92b, are identical in the present case. Moreover, a mechanical force path of the movement transducer 116b, by way of which a force is transmitted from the actuation train 106b to the further tool piece 94b, and an electrical conduction path of the movement transducer 116b, by way of which the further electrical potential is transmitted to the further tool piece 94b, are identical in the present case.

The movement transducer 116b is partially electrically conductive. For this purpose, the movement transducer 116b is made at least partially from a metal. The movement transducer 116b is formed partially from a further insulation material. The further insulation material has a CTI value of at least 150. In the present case, the further insulation material even has a CTI value of more than 600. The further insulation material can be PEEK, for example. In the present case, the further insulation material is a cycloolefin copolymer (COC) and/or polymethyl pentene. Only components of the movement transducer 116b that are configured to transmit movement from the actuation train 106b to the tool piece 92b are at least partially free of insulation material in order to let through the electrical potential. Only components of the movement transducer 116b that are configured to transmit movement from the actuation train 106b to the further tool piece 94b are at least partially free of insulation material in order to let through the further electrical potential.

For electrical connection, a push and/or pull piston 122b of the movement transducer 116b has at least one electrical pole conductor extension 194b. The electrical pole conductor extension 194b is electrically connected to the electrical pole conductor 184b of the actuation train 106b. Moreover, the electrical pole conductor extension 194b is mechanically connected to the electrical pole conductor 184b of the actuation train 106b.

The electrical pole conductor extension 194b extends partially through an armature 130b of the push and/or pull piston 122b. In the region of the armature 130b, the electrical pole conductor extension 194b is electrically and/or mechanically connected to a further component of the movement transducer 116b. Moreover, the electrical pole conductor extension 194b extends at least partially through a bolt 124b of the push and/or pull piston 122b. In the region of the bolt 124b, the electrical pole conductor extension 194b is electrically connected to the electrical pole conductor 184b.

The electrical pole conductor extension 194b has an electronic pole conductor extension main body 202. The electrical pole conductor extension 194b has a pole conductor sleeve 198b. The electrical pole conductor extension 194b is enclosed in the pole conductor sleeve 198b. The pole conductor sleeve 198b is arranged in the region of the bolt 124b of the push and/or pull piston 122b. The pole conductor sleeve 198b is firmly connected to a pole conductor extension main body 202b of the electrical pole conductor extension 194b. In the present case, the pole conductor sleeve 198b is welded to the pole conductor extension main body 202b.

The electrical pole conductor extension 194b is designed at least partially as a flat strip. The pole conductor extension main body 202b is designed as a flat strip. The electrical pole conductor extension 194b is made at least partially from metal. The pole conductor extension main body 202b can be sheet metal, for example.

The electrical pole conductor extension 194b is hook-shaped in a side view. The electrical pole conductor extension 194b engages at least partially around an additional guide slot 176b of the push and/or pull piston 122b. The electrical pole conductor extension 194b is designed at least partially as a sheet metal component, in particular a laser-cut sheet metal component. The pole conductor extension main body 202b is a sheet metal component, in particular a laser-cut sheet metal component. Alternatively, the electronic pole conductor extension could be an at least partially generatively produced component. For example, the electrical pole conductor extension could be produced by means of a laser melting and/or laser sintering method.

Moreover, the push and/or pull piston 122b has at least the further insulation material. The electrical pole conductor extension 194b is at least partially covered with the further insulation material. In the present case, the electrical pole conductor extension 194b is even at least largely covered with the further insulation material. In the present case, the further insulation material encapsulates the electrical pole conductor extension 194b. The electronic pole conductor extension 194b covered with the further insulation material forms at least partially the push and/or pull piston 122b.

For further electrical connection, the push and/or pull piston 122b of the movement transducer 116b has at least one further electrical pole conductor extension 196b. The further electrical pole conductor extension 196b is electrically connected to the further electrical pole conductor 186b of the actuation train 106b. Moreover, the further electrical pole conductor extension 196b is connected mechanically to the further electrical pole conductor 186b of the actuation train 106b.

The further electrical pole conductor extension 196b extends partially through the armature 130b of the push and/or pull piston 122b. In the region of the armature 130b, the further electrical pole conductor extension 196b is electrically and/or mechanically connected to a further component of the movement transducer 116b. Moreover, the further electrical pole conductor extension 196b extends at least partially through the bolt 124b of the push and/or pull piston 122b. In the region of the bolt 124b, the further electrical pole conductor extension 196b is electrically connected to the further electrical pole conductor 186b.

The further electrical pole conductor extension 196b has a further pole conductor extension main body 204b. The further electrical pole conductor extension 196b has a further pole conductor sleeve 198b. The further electrical pole conductor 186b is enclosed in the further pole conductor sleeve 200b. The further pole conductor sleeve 200b is arranged in the region of the bolt 124b of the push and/or pull piston 122b. The further pole conductor sleeve 200b is firmly connected to a further pole conductor extension main body 204b of the further electrical pole conductor extension 196b. In the present case, the further pole conductor sleeve 200b is welded to the further pole conductor extension main body 204b.

The further electrical pole conductor extension 196b is designed at least partially as a flat strip. The further pole conductor extension main body 204b is designed as a flat strip. The further electrical pole conductor extension 196b is made at least partially from metal. The further pole conductor extension main body 204b can be sheet metal, for example.

The further electrical pole conductor extension 196b is designed at least partially as a sheet metal component, in particular a laser-cut sheet metal component. The further pole conductor extension main body 204b is a sheet metal component, in particular a laser-cut sheet metal component. Alternatively, the further electrical pole conductor extension could be an at least partially generatively produced component. For example, the further electrical pole conductor extension could be produced by means of a laser melting and/or laser sintering method.

Moreover, the push and/or pull piston 122b has at least one further insulation material. In the present case, the latter is the aforementioned further insulation material. The further electrical pole conductor extension 196b is at least partially covered with the further insulation material. In the present case, the further electrical pole conductor extension 196b is even at least largely covered with the further insulation material. In the present case, the further insulation material encapsulates the further electrical pole conductor extension 196b. The further electrical pole conductor extension 196b covered with the further insulation material forms at least partially the push and/or pull piston 122b.

In a side view, the further electrical pole conductor extension 196b is designed corresponding to the electrical pole conductor extension 194b. The further electrical pole conductor extension 196b extends at least substantially parallel to the electrical pole conductor extension 194b. The electrical pole conductor extension 194b and the further electrical pole conductor extension 196b are arranged in the same plane. The plane can be a plane of symmetry of the push and/or pull piston 122b. The electrical pole conductor extension 194b engages at least partially around the further electrical pole conductor extension 196b.

In the present case, the further insulation material jointly encapsulates the electrical pole conductor extension 194b and the further electrical pole conductor extension 196b. The electrical pole conductor extension 194b and the further electrical pole conductor extension 196b are electrically insulated from each other by the further insulation material. The further insulation material, the electrical pole conductor extension 194b and the further pole conductor extension 196b at least largely form the push and/or pull piston 122b.

The movement transducer 116b has at least one pivot lever 132b. The pivot lever 132b is electrically connected to the push and/or pull piston 122b. The pivot lever 132b is electrically connected to the electrical pole conductor extension 194b. The pivot lever 132b has a pivot lever main body 134b. The pivot lever main body 134b is formed at least partially from metal. The pivot lever main body 134b is electrically connected to the tool piece 92b. The pivot lever 132b has at least one further insulation material. In the present case, the latter is the aforementioned further insulation material. The pivot lever main body 134b is covered at least partially by the further insulation material. In the present case, the pivot lever main body 134b is at least largely covered with the further insulation material.

The movement transducer 116b comprises at least one coupling mechanism 136b. The coupling mechanism 136b has at least one coupling element 138b. The coupling element 138b is part of the push and/or pull piston 122b. The coupling element 138b is electrically conductive. The coupling element 138b is made at least partially from metal. The coupling element 138b is at least partially free from the further insulation material which surrounds the push and/or pull piston 122b. Moreover, the coupling element 138b is mechanically operatively connected to the electrical pole conductor extension 194b. The coupling element 138b is electrically operatively connected to the electrical pole conductor extension 194b. For example, the coupling element 138b can be welded to the electrical pole conductor extension 194b.

The coupling mechanism 136b has at least one corresponding coupling element 140b. The corresponding coupling element 140b is part of a pivot lever 132b of the movement transducer 116b. The corresponding coupling element 140b is connected to a pivot lever main body 134b of the pivot lever 132b. The corresponding coupling element 140b is at least partially free from the further insulation material. The coupling element 138b and the corresponding coupling element 140b are electrically operatively connected to each other. The surfaces of the coupling element and of the corresponding coupling element 140b that bear on each other, and that are advantageously free from the further insulation material, form an electrical sliding contact.

The movement transducer 116b has at least one further pivot lever 150b (cf. FIG. 9). The further pivot lever 150b is electrically connected to the push and/or pull piston 122b. The further pivot lever 150b is electrically connected to the further electrical pole conductor extension 196b. The further pivot lever 150b has a further pivot lever main body 152b. The further pivot lever main body 152b is formed at least partially from metal. The further pivot lever main body 152b is electrically connected to the tool piece 92b. The further pivot lever 150b has at least one further insulation material. In the present case, the latter is the aforementioned further insulation material. The further pivot lever main body 152b is covered at least partially by the further insulation material. In the present case, the further pivot lever main body 152b is at least largely covered with the further insulation material.

The coupling mechanism 136b has at least one further coupling element 156b. The further coupling element 156b is part of the push and/or pull piston 122b. The further coupling element 156b is electrically conductive. The further coupling element 156b is formed at least partially from metal. The further coupling element 156b of the push and/or pull piston 122b is at least partially free from the further insulation material. The further coupling element 156b is electrically operatively connected to the further electrical pole conductor extension 196b. Moreover, the further coupling element 156b is mechanically operatively connected to the further electrical pole conductor extension 196b. For example, the further coupling element 156b is welded to the further electrical pole conductor extension 196b.

The coupling mechanism 136b has at least one further corresponding coupling element 158b. The corresponding coupling element 158b is part of the further pivot lever 150b. The further corresponding coupling element 158b is connected to a further pivot lever main body 152b of the further pivot lever 150b. The further corresponding coupling element 158b is at least partially free from the further insulation material. The further coupling element 156b and the further corresponding coupling element 158b are electrically operatively connected to each other. Surfaces of the further coupling element 156b and of the further corresponding coupling element 158b that bear on each other, and that are advantageously free from the further insulation material, form an electrical sliding contact.

Moreover, the end effector 90*b* has an end-effector head 96*b*. The end-effector head 96*b* is formed at least partially from a further insulation material, for example the aforementioned further insulation material. The end-effector head 96*b* has an end-effector main body 206*b*. In the present case, the end-effector main body 206*b* is formed at least partially from a metal. The end-effector main body 206*b* is at least largely covered with the further insulation material. In the present case, the end-effector main body 206*b* is covered completely with the further insulation material.

Components of the endoscopic device 16*b* that are covered with the further insulation material are covered seamlessly with the latter. For this purpose, main bodies of these components are encapsulated by injection with the further insulation material, for example the end-effector head, the end-effector fork, the push and/or pull piston, the pivot lever, the further pivot lever or the like. The further insulation material conforms snugly to further components, for example the tool piece, such that seams in which contamination could accumulate can advantageously be avoided.

FIG. 10 shows schematically at least one part of an alternative endoscopic device 16*c* in a sectional view along a shaft 26*c* of the endoscopic device 16*c*, according to the principles of the present disclosure in a sectional view along a shaft 26*c* of the endoscopic device 16*c* in a straight position. Moreover, FIG. 11 shows schematically at least one part of the endoscopic device 16*c* in a sectional view along the shaft 26*c* of the endoscopic device 16*c* in a deflection position. The present exemplary embodiment of the endoscopic device 16*c* differs from the preceding one essentially in terms of a deflection mechanism 46*c* of the endoscopic device 16*c*.

The deflection mechanism 46*c* has at least one first connection member 48*c*. In the present case, the deflection mechanism 46*c* has a plurality of first connection members. Moreover, the deflection mechanism 46*c* has at least one second connection member 50*c*. In the present case, the deflection mechanism 46*c* has a plurality of second connection members.

FIG. 10 shows the deflection mechanism 46*c* in a straight position. The first connection member 48*c* and the second connection member 50*c* are arranged relative to each other in a straight position. In the straight position, a first axis of rotational symmetry 52*c* of the first connection member 48*c* and a second axis of rotational symmetry 54*c* of the second connection member 50*c* are oriented at least substantially parallel to each other.

The first connection member 48*c* has a first geometric midpoint 64*c*. Moreover, the second connection member 50*c* has a second geometric midpoint 66*c*. In the straight position, the first geometric midpoint 64*c* and the second geometric midpoint 66*c* are arranged offset relative to each other.

When the first connection member 48*c* and the second connection member 50*c* are arranged in the straight position, a straight-position spacing 68*c* exists between the first connection member 48*c* and second connection member 50*c*. In the straight position, the straight-position spacing 68*c* is defined by a shortest connection between the first geometric midpoint 64*c* and second geometric midpoint 66*c*.

FIG. 11 shows the deflection mechanism 46*c* in a deflection position. The first connection member 48*c* and the second connection member 50*c* are arranged relative to each other in a deflection position. In the deflection position, the first axis of rotational symmetry 52*c* of the first connection member 48*c* and the second axis of rotational symmetry 54*c* of the second connection member 50*c* are arranged at an angle to each other. In the deflection position, an angle between the first axis of rotational symmetry 52*c* and the second axis of rotational symmetry 54*c* is at least 10°. In the deflection position, the first geometric midpoint 64*c* and the second geometric midpoint 66*c* are arranged offset relative to each other.

When the first connection member 48*c* and the second connection member 50*c* are arranged in the deflection position, a deflection spacing 70*c* exists between the first connection member 48*c* and second connection member 50*c*. In the deflection position, the deflection spacing 70*c* is defined by a shortest connection between the first geometric midpoint 64*c* and second geometric midpoint 66*c*. The deflection-position spacing 70*c* is greater than the straight-position spacing 68*c*.

In a deflection of the first connection member 48*c* and of the second connection member 50*c* relative to each other, as may occur for example during a transfer of the connection members from the straight position to the deflection position, they are configured such that their geometric midpoints 64*c*, 66*c* increases by at least 0.3 µm per degree of a deflection of these from the straight position. In the deflection position, there is a lengthening of the deflection mechanism 46*c* by comparison with the straight position. When the connection members 48*c*, 50*c* are pretensioned, for example by a control train of the endoscopic device 16*c*, the pretensioning in the deflection position increases compared to a pretensioning that acts on the connection members in the straight position. A restoring action can be achieved, as a result of which the connection members return automatically to a straight position.

In the present case, the deflection mechanism 46*c* has three first connection members 48*c*. Moreover, the deflection mechanism 46*c* has four second connection members 50*c*. By virtue of the arrangement of the plurality of first connection members and of the plurality of second connection members, a total of six interacting combinations of a first connection member and a second connection member are thus obtained.

The first connection member 48*c* has at least one outer contour 72*c*. The outer contour 72*c* is directed outward. The design of the outer contour 72*c* differs from concave. In the present case, the outer contour 72*c* is of convex design. The outer contour 72*c* describes an arc of a circle 76*c*. The outer contour 72*c* has at least partially a shape of a circle involute. Alternatively or in addition, the outer contour could accordingly have at least in part a shape of an arc of a circle, a cycloid, a paraboloid and/or an ellipsoid.

There exists a diameter 74*c* of a smallest conceivable arc of a circle 76*c* still just completely enclosing the outer contour 72*c* of the first connection member 48*c*. This diameter 74*c* is greater than a maximum connection member width 208*c* of the first connection member 48*c*. The connection member width 208*c* is measured at least substantially perpendicular to the direction of longitudinal extent 38*c* of a shaft 26*c* of the endoscopic device 16*c*.

The second connection member 50*c* has at least one inner contour 78*c*. The inner contour 78*c* is directed inward. The design of the inner contour 78*c* differs from concave. Moreover, in the present case, the inner contour 78*c* is straight. The inner contour 78*c* is at least partially different from an arc of a circle 76*c*. Alternatively or in addition, the inner contour could accordingly have at least in part a shape of an arc of a circle, a circle involute, a cycloid, a paraboloid and/or an ellipsoid.

The outer contour 72*c* and the inner contour 78*c* lie opposite each other. The inner contour 78*c* of the second connection member 50c is configured for interaction with the outer contour 72c of the first connection member 48c, and vice versa. The outer contour 72c and the inner contour 78c bear at most partially on each other.

FIG. 12 shows a schematic perspective view of at least one part of a further exemplary embodiment of a further endoscopic device 16d in an assembly state, according to the principles of the present disclosure. Moreover, FIGS. 13 and 14 show further assembly states of the endoscopic device 16d. The present exemplary embodiment of the endoscopic device 16d differs from the preceding one essentially in terms of a deflection mechanism 46d of the endoscopic device 16d.

The deflection mechanism 46d has at least one control train 80d. The control train 80d is connected to an end portion 28d of the shaft 26d. A part of the control train 80d is arranged forming a loop-back 84d in the region of the end portion 28d of the shaft 26d. The loop-back 84d has a loop-back radius 212d. The loop-back radius 212d is greater than the diameter 74d of the control train 80d. The loop-back radius 212d is at least twice as great as the diameter 74d of the control train 80d.

The end portion 28d of the shaft 26d has at least one loop-back guide 210d. The control train 80d is arranged at least partially in the loop-back guide 210d. A portion of the control train 80d forming the loop-back 84d is arranged in the loop-back guide 210d. In a side view, the loop-back guide 210d has a keyhole-shaped contour. Before the loop-back 84d, a loop-back guide 210d guides the control train 80d in the direction of the end portion 28d of the shaft 26d. After the loop-back 84d, the loop-back guide 210d guides the control train 80d back toward the end portion 28d of the shaft 26d.

The loop-back guide 210d guides the control train 80d at least in part substantially parallel to an axis of principal extent 120d of the shaft 26d. There exists a smallest spacing between a portion guided to the loop-back 84d and a portion of the control train 80d guided back from the loop-back 84d. This smallest spacing is smaller than twice the loop-back radius 212d of the loop-back 84d or the loop-back guide 210d.

The loop-back guide 210d has an angle of circumferential extent 214d. The angle of circumferential extent 214d is an angle that describes the radial angle part of the loop-back 84d. The angle of circumferential extent 214d measures more than 180°. In the present case, the angle of circumferential extent 214d measures at least 210°. Moreover, the angle of circumferential extent 214d has an angle of less than 360°. In the present case, the angle of circumferential extent 214d is at most 340°.

For radial insertion of the control train 80d into the loop-back guide 210d, the latter is radially opened to the outside. Alternatively, the loop-back guide could be opened to the inside. It is also conceivable that the loop-back guide can be covered radially outwardly by means of a covering. For this purpose, a covering could be able to be coupled to an end portion of a shaft. The covering at least partially covers an end portion 28d of the shaft 26d, in order to close the loop-back guide 210d radially to the outside.

Moreover, the end portion 28d has a plurality of loop-back guides 210d, which are arranged offset relative to one another along the circumference of the shaft 26d. Of the plurality of loop-back guides, for the sake of clarity only the loop-back guide 210d is provided with a reference sign. A plurality of control trains are arranged in the plurality of loop-back guides. Here, one control train 80d is arranged in each one of the plurality of loop-back guides.

FIG. 13 shows a schematic perspective view of at least one part of an additional endoscopic device 16e in an assembly state, according to the principles of the present disclosure. FIG. 14 shows a schematic perspective view of the part of the endoscopic device 16e in an additional assembly state. FIG. 15 moreover shows a schematic perspective view of at least the part of the further endoscopic device 16e in a mounted state. The present exemplary embodiment of the further endoscopic device 16e differs from the preceding ones essentially in terms of a deflection mechanism 46e of the endoscopic device 16e.

The deflection mechanism 46e has at least one first connection member 48e. Moreover, the deflection mechanism 46e has at least one second connection member 50e.

The second connection member 50e has at least one passageway 82e. Moreover, the second connection member 50e has at least one radial opening 216e. The radial opening 216e is connected to the passageway 82e. A control train 80e is insertable into the passageway 82e via the radial opening 216e.

The second connection member 50e has at least one connection member main body 218e. The connection member main body 218e has the radial opening 216e. Moreover, the connection member main body 218e has the passageway 82e. The connection member main body 218e has a connection recess 220e. The connection recess 220e extends at least partially radially. In the present case, the connection recess 220e extends completely radially. The connection recess 220e of the connection member main body 218e connects the passageway 82e and the radial opening 216e to each other.

The second connection member 50e has at least one closure body 222e. The closure body 222e is configured to close the radial opening 216e at least in an inserted state of the control train 80e. In the present case, the closure body 222e is designed as a clamping ring. The closure body 222e is connectable to the connection member main body 218e. In the present case, the closure body 222e is connectable to the connection member main body 218e by force-fit and/or form-fit engagement. Moreover, the closure body 222e is cohesively bonded or welded to the connection member main body 218e.

FIG. 16 shows a schematic plan view of at least one part of an alternative endoscopic device 16f according to the principles of the present disclosure. The present exemplary embodiment of the endoscopic device 16f differs from the preceding one essentially in terms of a configuration of a deflection mechanism 46f of the endoscopic device 16f.

A second connection member 50f of the deflection mechanism 46f has at least one connection member main body 218f. The connection member main body 218f has at least one passageway 82f. Moreover, the connection member main body 218f has at least one radial opening 216f. Moreover, the connection member main body 218f has a connection recess 220f. The connection recess 220f connects the radial opening 216f to the passageway 82f.

In the present case, the connection recess 220f extends radially in part. The connection recess 220f describes a curved path. In the present case, the radially extending recess describes a hook-shaped curved path. The connection recess 220f has the shape of a curved path. The curved path has a curved-path angle of more than 90°. In the present case, the curved path has a curved-path angle of more than 150°. Moreover, the curved-path angle is at most 180°. Advantageously, it is possible to dispense here with a closure body according to the preceding exemplary embodiment.

FIG. 17 shows a schematic perspective view of at least one part of an alternative endoscopic device 16g according to the principles of the present disclosure. The present exemplary embodiment differs from the preceding ones essentially in terms of a configuration of a deflection mechanism 46g of the endoscopic device 16g.

A second connection member 50g of the deflection mechanism 46g has at least one connection member main body 218g. The connection member main body 218g has at least one passageway 82g. Moreover, the connection member main body 218g has at least one radial opening 216g. Moreover, the connection member main body 218g has a connection recess 220g. The connection recess 220g connects the radial opening 216g to the guide hole.

In the present case, the radial opening 216g extends at an angle to an axis of rotational symmetry of the second connection member. Moreover, the radial opening 216g can have a profile like a curved path. For example, in such a profile, a continuous profile can correspond approximately to a cosine wave.

FIG. 18 shows a schematic perspective view of at least one part of an alternative endoscopic device 16h in an assembly state according to the principle of the present disclosure. FIG. 19 shows a schematic perspective view of the part of the endoscopic device 16h in a mounted state. Moreover, FIG. 20 shows a schematic perspective view of the part of the endoscopic device 16h in an assembly state. Moreover, FIG. 21 shows a schematic perspective view of the part of the endoscopic device 16h in a further assembly state. FIG. 22 shows a schematic perspective view of at least the part of the endoscopic device 16h in a mounted state. The present exemplary embodiment of the endoscopic device 16h differs from the preceding ones essentially in terms of a configuration of a deflection mechanism 46h of the endoscopic device 16h.

The deflection mechanism 46h has a second connection member 50h. The connection member 50h comprises at least one connection member main body 218h. The connection member main body 218h has at least one passageway 82h. Moreover, the connection member main body 218h has a radial opening 216h. Moreover, the connection member main body 218 comprises a connection recess 220h. The connection recess 220h connects the radial opening 216h to the passageway 82h.

A second connection member has at least one further connection member main body 224h. The further connection member main body 224h has at least one further passageway 226h. In the present case, the connection member main body 218h and the further connection member main body 224h are at least substantially identical to each other. Moreover, the further connection member main body 224h has a further radial opening 228h. Moreover, the further connection member main body 224h has a further connection recess 230h. The further connection recess 230h connects the further radial opening 228h to the further passageway 226h.

The connection member main body 218h and the further connection member main body 224h can be coupled to each other. The connection member main body 218h and the further connection member main body 224h are connectable to each other by force-fit and/or form-fit engagement. In a position in which a radial opening 216h of the connection member main body 218h and the further radial opening 228h of the further connection member main body 224h are congruent with each other, the connection member main body 218h and the further connection member main body 224h are separated from each other.

In a further position, in which the passageway 82h of the connection member main body 218h and the further passageway 226h of the further connection member main body 224h are congruent with each other, the connection member main body 218h and the further connection member main body 224h are connectable to each other. A control train 80e of the deflection mechanism 46h keeps the connection member main body 218h and the further connection member main body 224h pretensioned in a mounted state, such that these are pressed together. Alternatively or in addition, the connection member main bodies could be connectable by means of a quick connector 248h, for example a bayonet closure, a screw closure or the like.

FIG. 23 shows a schematic side view of at least one part of an alternative endoscopic device 16i in a straight position according to the principles of the present disclosure. Moreover, FIG. 24 shows schematically the part of the endoscopic device 16i from FIG. 23 in a sectional view along a shaft 26i of the endoscopic device 16i in the straight position. FIG. 25 shows a schematic side view of the part of the endoscopic device 16i in a deflection position. FIG. 26 shows schematically the part of the endoscopic device 16i in a sectional view along the shaft 26i of the endoscopic device 16i in the deflection position. The present exemplary embodiment of the endoscopic device 16i differs from the preceding one essentially in terms of a deflection mechanism 46i of the endoscopic device 16i.

The deflection mechanism 46i has at least one first connection member 48i. In the present case, the deflection mechanism 46i has a plurality of first connection members. Moreover, the deflection mechanism 46i has at least one second connection member 50i. In the present case, the deflection mechanism 46i has a plurality of second connection members.

The first connection member 48i is formed at least partially from a first material 232i. The first material 232i is assigned to the substance group of plastics. In the present case, the first material 232i is an elastomer. The first material 232i has a first elasticity.

The second connection member 50i is formed at least partially from a second material 234i. The second material 234i is assigned to the substance group of plastics. The second material 234i is a thermoplastic. Alternatively, the second material could also be a metal, a ceramic or the like.

The second material 234i has a second elasticity. The second elasticity of the second material 234i differs from the first elasticity of the first material 232i. In the present case, an elasticity of the first material 232i is greater than an elasticity of the second material 234i.

The second connection member 50i is arranged at least partially coaxially surrounding the first connection member 48i. The first connection member 48i has a tubular design. The second connection member 50i has a ring-like design.

The first connection member 48i and the second connection member 50i are connected to each other at least by form-fit engagement. The first connection member 48i and the second connection member 50i engage at least partially in each other in an engagement region 236i. The first connection member 48i has a first profiling 238i for connecting it to the second connection member 50i. In the present case, the profiling 238i has the form of an undulation. The second connection member 50i has a second profiling 240i for connecting it to the first connection member 48i. The second profiling 240i is designed corresponding to the first profiling 238i. For an at least form-fit connection of the first connection member 48i and of the second connection member 50*i*, the first profiling 238*i* and the second profiling 240*i* engage in each other and form the engagement region 236*i*.

Moreover, the first connection member 48*i* and the second connection member 50*i* are connected to each other by at least cohesive bonding. For example, the first connection member 48*i* and the second connection member 50*i* could be adhesively fixed to each other. In the present case, however, the first connection member 48*i* and the second connection member 50*i* are injected onto each other. In this way, at least the first connection member 48*i* and the second connection member 50*i* at least partially form a multi-component injection molded assembly 242*i* of the endoscopic device 16*i*.

In the present case, the plurality of first connection members are formed integrally with one another. The plurality of first connection members together form a hose. The principal extent of the hose corresponds at least substantially to a principal extent of a deflection mechanism 46*i* of the endoscopic device 16*i*. The plurality of second connection members are then in each case arranged offset relative to each other about the hose. Thus, the plurality of first connection members and the plurality of second connection members together form the multi-component injection molded assembly 242*i*.

FIG. 27 shows a schematic perspective view of at least one part of a further endoscopic device 16*j* according to the principles of the present disclosure. The present exemplary embodiment of the endoscopic device 16*j* differs from the preceding ones essentially in terms of a modular configuration of the endoscopic device 16*j*.

The endoscopic device 16*j* has at least one end-effector module 244*j*. The end-effector module 244*j* comprises at least one end effector 90*j*. Moreover, the end-effector module 244*j* has an actuation train 106*j*. Moreover, the end-effector module 244*j* has a movement transducer 116*j*. The end-effector module 244*j* is designed as a re-usable module. For example, the end-effector module 244*j* is configured so as to be autoclavable, such that it can be cleaned after an intervention and thus used a number of times. Alternatively, the end-effector module could be designed as a disposable module. For example, the end-effector module could be designed so as not to be autoclavable. It would be conceivable that, if an attempt is made to re-use it, the disposable module deliberately presents a defect, which impedes its function or detects and indicates repeat use.

The endoscopic device 16*j* moreover comprises at least one shaft module 246*j*. The shaft module 246*j* has at least the shaft 26*j*. Moreover, the shaft module 246*j* has a deflection mechanism 46*j*. The shaft module 246*j* is designed as a disposable module. For example, the shaft module 246*j* could be designed so as not to be autoclavable. It would be conceivable that, if an attempt is made to re-use it, the disposable module deliberately presents a defect, which impedes its function or detects and indicates repeat use. Alternatively, the shaft module could be designed as a re-usable module. For example, the shaft module is configured to be autoclavable, such that it can be cleaned after an intervention and can thus be used a number of times. Moreover, the shaft module 246*j* can have all the components of the endoscopic device 16*j* that are not already assigned to the end-effector module 244*j*.

The end-effector module 244*j* and the shaft module 246*j* are exchangeably connectable to each other. The endoscopic device 16*j* comprises at least one quick connector 248*j*. In the present case, the quick connector 248*j* is designed as a screw connector. Alternatively, the quick connector could also be a snap-fit connection, a clamping connection, a bayonet connection or the like.

The quick connector 248*j* has a quick-connector piece 250*j*. Moreover, the quick connector 248*j* has a quick-connector piece 252*j* corresponding to the quick-connector piece 250*j*. In the present case, the quick-connector piece 250*j* is a threaded piece. The quick-connector piece 250*j* has an inner thread. In the present case, the corresponding quick-connector piece 252*j* is a corresponding threaded piece. The corresponding quick-connector piece 252*j* has an outer thread.

The quick connector 248*j* is at least partially connected integrally to the end effector 90*j*. An end-effector head 96*j* of the end effector 90*j* is formed integrally with the quick connector 248*j*. In the present case, the end portion 28*j* of the shaft 26*j* has the corresponding quick-connector piece 252*j*. Moreover, the quick connector 248*j* is at least partially formed by an end-effector head 96*j* of the end effector 90*j*. In the present case, the end-effector head 96*j* has the corresponding quick-connector piece 252*j*.

In order to achieve exchangeability and thus variability of use, the endoscopic device 16*j* has at least one or more further end-effector modules. Moreover, the endoscopic device 16*j* can have at least one or more further shaft modules 246*j*.

| | |
|---|---|
| 10 | surgical system |
| 12 | surgical robot |
| 14 | controller |
| 16 | endoscopic device |
| 18 | robot arm |
| 20 | endoscopic instrument |
| 22 | endoscope |
| 26 | shaft |
| 28 | end portion |
| 30 | further end portion |
| 32 | middle portion |
| 34 | main framework |
| 36 | shaft jacket |
| 38 | direction of longitudinal extent |
| 40 | longitudinal extent |
| 42 | deflectable portion |
| 44 | plane |
| 46 | deflection mechanism |
| 48 | first connection member |
| 50 | second connection member |
| 52 | first axis of rotational symmetry |
| 54 | second axis of rotational symmetry |
| 56 | cuff |
| 58 | further cuff |
| 60 | joint head |
| 62 | joint socket |
| 64 | first geometric midpoint |
| 66 | second geometric midpoint |
| 68 | straight-position spacing |
| 70 | deflection-position spacing |
| 72 | outer contour |
| 74 | diameter |
| 76 | arc of a circle |
| 78 | inner contour |
| 80 | control train |
| 82 | passageway |
| 84 | loop-back |
| 86 | train receptacle |
| 88 | passageway |
| 90 | end effector |
| 92 | tool piece |
| 94 | further tool piece |
| 96 | end-effector head |
| 98 | end-effector fork |
| 100 | end-effector limb |
| 102 | further end-effector limb |
| 104 | end-effector bushing |
| 106 | actuation train |

| | |
|---|---|
| 108 | flexible portion |
| 110 | inflexible portion |
| 112 | inner cable |
| 114 | reinforcement |
| 116 | movement transducer |
| 118 | pivot axis |
| 120 | axis of principal extent |
| 122 | push and/or pull piston |
| 124 | bolt |
| 126 | piston guide |
| 128 | actuation train receptacle |
| 130 | armature |
| 132 | pivot lever |
| 134 | pivot lever main body |
| 136 | coupling mechanism |
| 138 | coupling element |
| 140 | corresponding coupling element |
| 142 | rotary bearing |
| 144 | bearing element |
| 146 | corresponding bearing element |
| 148 | rotary axis |
| 150 | further pivot lever |
| 152 | further pivot lever main body |
| 154 | further coupling mechanism |
| 156 | further coupling element |
| 158 | further corresponding coupling element |
| 160 | further pivot axis |
| 162 | further rotary bearing |
| 164 | further bearing element |
| 166 | further corresponding bearing element |
| 168 | further rotary axis |
| 170 | guide bearing |
| 172 | slotted guide |
| 174 | further slotted guide |
| 176 | additional slotted guide |
| 178 | guide pin |
| 180 | pin receptacle |
| 182 | further pin receptacle |
| 184 | electrical pole conductor |
| 186 | further electrical pole conductor |
| 188 | outer cable |
| 190 | electrical insulator |
| 192 | further electrical insulator |
| 194 | electrical pole conductor extension |
| 196 | further electrical pole conductor extension |
| 198 | pole conductor sleeve |
| 200 | further pole conductor sleeve |
| 202 | pole conductor extension main body |
| 204 | further pole conductor extension main body |
| 206 | end-effector main body |
| 208 | connection member width |
| 210 | loop-back guide |
| 212 | loop-back radius |
| 214 | angle of circumferential extent |
| 216 | radial opening |
| 218 | connection member main body |
| 220 | connection recess |
| 222 | closure body |
| 224 | further connection member main body |
| 226 | further passageway |
| 228 | further radial opening |
| 230 | further connection recess |
| 232 | first material |
| 234 | second material |
| 236 | engagement region |
| 238 | first profiling |
| 240 | second profiling |
| 242 | multi-component injection molded assembly |
| 244 | end-effector module |
| 246 | shaft module |
| 248 | quick connector |
| 250 | quick-connector piece |
| 252 | corresponding quick-connector piece |

We claim:

1. An endoscopic device having at least one shaft, which has at least one portion deflectable in at least one plane, and having at least one deflection mechanism, which is configured to deflect the deflectable portion and comprises, arranged in series, at least one first connection member and at least one second connection member interacting for a deflection with the first connection member, wherein, when the first connection member and the second connection member are arranged in a straight position relative to each other, a straight-position spacing exists which is defined by a shortest connection between a geometric midpoint of the first connection member and a geometric midpoint of the second connection member, and, when the first connection member and the second connection member are arranged in a deflection position relative to each other, a deflection-position spacing exists which is defined by a shortest connection between a geometric midpoint of the first connection member and a geometric midpoint of the second connection member, and the deflection-position spacing of the connection members in the deflection position is greater than the straight-position spacing of the connection members in the straight position.

2. The endoscopic device as claimed in claim 1, wherein a spacing between the geometric midpoints of the connection members increases at least by 0.3 μm per degree of a deflection of these from the straight position.

3. The endoscopic device as claimed in claim 1, wherein the first connection member has at least one outer contour and the second connection member has at least one inner contour interacting with the outer contour of the first connection member, wherein the inner contour and/or the outer contour are/is other than concave.

4. The endoscopic device as claimed in claim 3, wherein the outer contour and/or the inner contour are convex.

5. The endoscopic device as claimed in claim 3, wherein the outer contour and the inner contour bear at most in part on each other.

6. The endoscopic device as claimed in claim 3, wherein a diameter of a smallest arc of a circle still completely enclosing the outer contour is greater than a connection member width of the first connection member measured perpendicularly to a principal extent of the shaft.

7. The endoscopic device as claimed in claim 3, wherein the outer contour and/or the inner contour are/is at least in part different from an arc of a circle.

8. The endoscopic device as claimed in claim 3, wherein the outer contour and/or the inner contour are/is designed corresponding at least in part to a shape of an arc of a circle, a circle involute, a cycloid, a paraboloid and/or an ellipsoid.

9. The endoscopic device as claimed in claim 1, wherein it comprises at least one flexurally slack control train on which the connection members are arranged in rows and which, in the straight position of the connection members, keeps the connection members pretensioned.

10. The endoscopic device as claimed in claim 1, wherein the deflection mechanism has a number of first connection members and a number of second connection members, wherein a difference between the number of the first connection members and the number of the second connection members, is different than zero.

11. An endoscope and/or endoscopic instrument having an endoscopic device as claimed in claim 1.

12. A surgical system having at least one endoscopic device as claimed in claim 1 and having at least one surgical robot.

13. A method for operating and/or for producing an endoscopic device as claimed in claim 1.

14. The endoscopic device as claimed in claim 1, wherein the at least one portion deflectable is positioned at a distal end of the shaft.

* * * * *